United States Patent
June et al.

(10) Patent No.: US 7,175,843 B2
(45) Date of Patent: *Feb. 13, 2007

(54) METHODS FOR SELECTIVELY STIMULATING PROLIFERATION OF T CELLS

(75) Inventors: Carl H. June, Merion Station, PA (US); Craig B. Thompson, Merion, PA (US); Gary J. Nabel, Washington, DC (US); Gary S. Gray, Brookline, MA (US); Paul D. Rennert, Holliston, MA (US)

(73) Assignees: Genetics Institute, LLC, Cambridge, MA (US); Regents of the University of Michigan, Ann Arbor, MI (US); The United States of America as represented by the Secretary of the Navy, Washington, DC (US)

( * ) Notice: Subject to any disclaimer, the term of this patent is extended or adjusted under 35 U.S.C. 154(b) by 26 days.

This patent is subject to a terminal disclaimer.

(21) Appl. No.: 11/366,331

(22) Filed: Mar. 2, 2006

(65) Prior Publication Data
US 2006/0140919 A1    Jun. 29, 2006

Related U.S. Application Data

(63) Continuation of application No. 08/253,964, filed on Jun. 3, 1994, now abandoned.

(51) Int. Cl.
*A61K 35/14* (2006.01)
*A61K 35/26* (2006.01)
*A61K 35/28* (2006.01)

(52) U.S. Cl. ............ 424/93.71; 424/93.1; 424/93.7; 424/534; 424/577; 424/578; 435/2; 435/375; 435/377

(58) Field of Classification Search .......... None
See application file for complete search history.

(56) References Cited

U.S. PATENT DOCUMENTS

| | | | |
|---|---|---|---|
| 4,654,210 A | 3/1987 | Kung et al. | |
| 5,004,681 A | 4/1991 | Boyse et al. | |
| 5,081,029 A | 1/1992 | Zarling et al. | |
| 5,500,348 A | 3/1996 | Nishimura et al. | |
| 5,521,288 A | 5/1996 | Linsley et al. | |
| 5,601,819 A | 2/1997 | Wong et al. | |
| 5,696,079 A | 12/1997 | Lane et al. | |
| 5,858,358 A | 1/1999 | June et al. | |
| 5,872,222 A | 2/1999 | Chang | |
| 5,883,223 A | 3/1999 | Gray | |
| 6,010,902 A | 1/2000 | Ledbetter et al. | |
| 6,129,916 A | 10/2000 | Chang | |
| 6,352,694 B1 | 3/2002 | June et al. | |
| 6,534,055 B1 | 3/2003 | June et al. | |
| 6,797,514 B2 | 9/2004 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 2002/0076407 A1 | 6/2002 | June et al. | |
| 2004/0001829 A1 | 1/2004 | June et al. | |
| 2006/0013832 A1 | 1/2006 | June et al. | |

FOREIGN PATENT DOCUMENTS

| | | |
|---|---|---|
| EP | 0 360 205 | 3/1990 |
| EP | 0 440 373 | 8/1991 |
| EP | 0 448 057 | 9/1991 |
| JP | 02-502424 | 8/1990 |
| JP | 04-502009 | 4/1992 |
| WO | WO88/07077 | 9/1988 |
| WO | WO-90/05541 | 5/1990 |
| WO | WO-92/00092 | 1/1992 |
| WO | WO-93/19767 | 10/1993 |
| WO | WO-94/12196 | 6/1994 |
| WO | WO-94/29436 | 12/1994 |
| WO | WO-95/33823 | 12/1995 |

OTHER PUBLICATIONS

U.S. Appl. No. 08/253,964, June et al.
U.S. Appl. No. 09/553,865, June et al.
U.S. Appl. No. 11/326,148, June et al.
U.S. Appl. No. 11/364,102, June et al.
Abbas et al., Cellular and Molecular Immunology 2nd Edition.
Allen et al., Blood vol. 81, No. 12, pp. 3242-3251, Jun. 15, 1993.
Asjo et al., Journal of Virology vol. 67, No. 7, pp. 4395-4398, Jul. 1993.
Axelrod et al., Proceedings of the National Academy of Sciences of the United States of America (Genetics) vol. 87, pp. 5173-5177, Jul. 1990.
Azuma et al., Journal of Experimental Medicine vol. 177, pp. 845-850 (1993).
Baier et al., Nature vol. 378, Dec. 7, 1995.

(Continued)

*Primary Examiner*—Phillip Gambel
(74) *Attorney, Agent, or Firm*—Wilmer Cutler Pickering Hale and Dorr LLC

(57) ABSTRACT

Methods for inducing a population of T cells to proliferate by activating the population of T cells and stimulating an accessory molecule on the surface of the T cells with a ligand which binds the accessory molecule are described. T cell proliferation occurs in the absence of exogenous growth factors or accessory cells. T cell activation is accomplished by stimulating the T cell receptor (TCR)/CD3 complex or the CD2 surface protein. To induce proliferation of an activated population T cells, an accessory molecule on the surface of the T cells, such as CD28, is stimulated with a ligand which binds the accessory molecule. The T cell population expanded by the method of the invention can be genetically transduced and used for immunotherapy or can be used in methods of diagnosis.

65 Claims, 18 Drawing Sheets

OTHER PUBLICATIONS

Ballen et al., Adoptive immunotherapy pp. 579-583.
Baroja et al., Cellular Immunology vol. 120, pp. 205-217, (1989).
Baroja et al., The Journal of Immunology vol. 141, No. 5, pp. 1502-1507, Sep. 1, 1988.
Basse et al., Cancer Immunology Immunotherapy pp. 221-227 (1992).
Belldegrun et al., Cancer Research vol. 48, pp. 206-214, Jan. 1, 1988.
Blair et al., Journal of Experimental Medicine vol. 191(4):651-660, 2000.
Bordignon et al., Proceedings of the National Academy of Sciences of the United States of America (Medical Sciences) vol. 86, pp. 6748-6752, Sep. 1989.
Boucheix et al., The Journal of Biological Chemistry vol. 266, No. 1, pp. 117-122 (1991).
Carroll et al., Biochemical Journal vol. 266, pp. 527-535 (1990).
Chow et al., Nature vol. 361, pp. 650-654, Feb. 18, 1993.
Cocchi et al., Science vol. 270, pp. 1811-1815, Dec. 15, 1995.
Cosimi et al., Transplantation vol. 32, No. 6, pp. 535-539, 1981.
Creson et al., Journal of Virology vol. 73, No. 11, pp. 9337-9347 (1999).
Damle et al., The Journal of Immunology vol. 140, No. 6, pp. 1753-1761, Mar. 15, 1988.
Damle et al., The Journal of Immunology vol. 143, No. 6, pp. 1761-1767, Sep. 15, 1989.
Diegel et al., AIDS Research and Human Retroviruses vol. 9, No. 5, pp. 465-473, 1993.
Drumm et al., Cell vol. 62, pp. 1227-1233.
Fahey et al., Clin. Exp. Immunol. vol. 88, pp. 1-5, 1992.
Fink et al., Proceedings of the National Academy of Sciences of the United States of America (Genetics) vol. 87, pp. 2334-2338, Mar. 1990.
Freedman et al., Cellular Immunology vol. 137, pp. 429-437, (1991).
Galvin et al., Journal of Immunology vol. 149, No. 12, pp. 3802-3808, Dec. 15, 1992.
Garbrecht et al., Journal of Immunological Methods vol. 107, pp. 137-142 (1988).
Geppert et al., The Journal of Immunology vol. 138, pp. 1660-1666, (1987).
Groux et al., Journal of Experimental Medicine vol. 175, pp. 331-340, Feb. 1992.
Gruters et al., European Journal of Immunology vol. 21, pp. 167-172, 1991.
Guinan et al., Blood vol. 84, pp. 3261-3282, 1994.
Hansen et al., Immunogenetics vol. 10, pp. 247-260, (1980).
Hara et al., Journal of Experimental Medicine vol. 161, pp. 1513-1524, Jun. 1985.
Harding et al., Nature vol. 356, pp. 607-609, Apr. 1992.
Haynes et al., Ann. Med.: Trends in Molecular Medicine vol. 28, pp. 39-41, 1996.
Hellstrom et al., Proceedings of the National Academy of Science vol. 98, pp. 6783-6788 (2001).
Hirsch et al., The New England Journal of Medicine pp. 1686-1695, 1993.
Hirshaut et al., Cancer vol. 56, pp. 1366-1373, 1985.
Human Gene Therapy 5: pp. 603-614 (1994).
Jennings et al., Journal of Biological Chemistry vol. 265, No. 7, pp. 3815-3822, Mar. 5, 1990.
Johnson et al., The Journal of Immunology vol. 152, No. 2, 429-437, Jan. 15, 1994.
Jong et al, Immunology vol. 74, pp. 175-182, (1991).
June et al., Immunology Today vol. 11, No. 6, pp. 211-216, 1990.
June et al., Molecular and Cellular Biology vol. 7, No. 12, pp. 4472-4481, Dec. 1987.
June et al., The Journal of Immunology vol. 143, No. 1, pp. 153-161, Jul. 1, 1989.
Jung et al., Proceedings of the National Academy of Sciences vol. 84, No. 13, Jul. 1987.
Kalinski et al., The Journal of Immunology vol. 154, pp. 3753-3760, 1995.
Kantoff et al., Proceedings of the National Academy of Sciences vol. 83, pp. 6563-6567, 1986.
Kimmel et al., Journal of Neurosurgery vol. 66, pp. 161-171 (1987).
King et al., European Journal of Immunology vol. 25, pp. 587-595, 1995.
Kmiec, American Scientist: Gene Therapy vol. 87, pp. 240-247 (1999).
Koulova et al., The Journal of Immunology vol. 145, No. 7, pp. 2035-2043, Oct. 1, 1990.
Kozbor et al., The Journal of Immunology vol. 138, pp. 4128-4132 (1987).
Lanza et al., Journal of Biological Chemistry vol. 266, No. 16, pp. 10638-10645, Jun. 5, 1991.
Lea et al., Journal of Molecular Recognition vol. 1, pp. 9-18 (1988).
Ledbetter et al., Blood vol. 75, No. 7, pp. 1531-1539, Apr. 1, 1990.
Ledbetter et al., European Journal of Immunology vol. 18, pp. 1601-1608, 1988.
Ledbetter et al., Proceedings of the National Academy of Sciences (Immunology), vol. 84, pp. 1384-1388, Mar. 1987.
Ledbetter et al., Proceedings of the National Academy of Sciences (Immunology), vol. 85, pp. 8628-8632, Nov. 1988.
Ledbetter et al., The Journal of Immunology vol. 135, No. 4, pp. 2331-2336, Oct. 1985.
Ledbetter et al., The Journal of Immunology vol. 137, No. 10, pp. 3299-3305, Nov. 15, 1986.
Lederman et al., Molecular Immunology vol. 18, pp. 1171-1181, 1991.
Lee et al., Advances in Regulation of Cell Growth, vol. 2; Cell Activation: Genetic Approaches vol. 2, Chapter 7, pp. 141-160, (1991).
Lesslauer et al., European Journal of Immunology vol. 16, pp. 1289-1296, 1986.
Levine et al., Science vol. 272, pp. 1939-1943, Jun. 28, 1996.
Levine et al., The Journal of Immunology pp. 5921-5930, 1997.
Li et al., Proceedings of the National Academy of Science vol. 77, pp. 3211-3214 (1990).
Linsley et al., Journal of Experimental Medicine vol. 173, pp. 721-730, Mar. 1991.
Lyerty et al., Aids Research and Human Retroviruses vol. 3, pp. 87-94, 1987.
Malik et al., Blood vol. 86, (1995).
Malim et al., Journal of Experimental Medicine vol. 176, pp. 1197-1201 (1992).
Martin et al., The Journal of Immunology vol. 136, No. 9, pp. 3282-3287, May 1, 1986.
McArthur et al., Journal of Experimental Medicine vol. 178, pp. 1645-1653, Nov. 1993.
Miller et al., Proceedings of the National Academy of Sciences of the United States of America (Biochemistry) vol. 80, pp. 4709-4713, Aug. 1983.
Miyanohara et al., Proceedings of the National Academy of Sciences of the United States of America (Medical Sciences) vol. 85, pp. 6538-6542, Sep. 1988.
Moran et al., AIDS Research and Human Retroviruses vol. 9, No. 5, pp. 455-464, 1993.
Ngo et al., The Protein Folding Problem and Tertiary Structure Prediction Chapter 14,, pp. 433-506 (1994).
Norton et al., The Journal of Immunology vol. 149, No. 5, pp. 1556-1561, Sep. 1, 1992.
Ochard et al., Human Gene Therapy vol. 13, pp. 979-988 (2002).
Osband et al., Immunology Today vol. 11, pp. 193-195, (1990).
Osborne et al., Proceedings of the National Academy of Sciences of the United States of America (Genetics) vol. 85, pp. 6851-6855, Sep. 1988.
Palmer et al., Proceedings of the National Academy of Sciences of the United States of America (Genetics) vol. 84, pp. 1055-1059, Feb. 1987.
Pene et al., Journal of Immunological Methods vol. 283, pp. 59-66 (2003).
Pemo et al., The Journal of Experimental Medicine vol. 168, pp. 1111-1125, Sep. 1988.
Perrin et al., Blood Suppl. P. 439a, No. 1747, 1991.

Pierres et al., European Journal of Immunology vol. 18, pp. 685-690, 1988.
Pierres et al., The Journal of Immunology vol. 144, No. 4, pp. 1202-1207, Feb. 15, 1990.
Pinchuk et al., Immunity vol. 1, pp. 317-325, Jul. 1994.
Poggi et al. European Journal of Immunology pp. 1065-1068 (1987).
Ramsay et al., Journal of Clinical Immunology vol. 8, No. 2, 81-88, 1988.
Reiser et al., Proceedings of the National Academy of Science vol. 89, pp. 271-275, Jan. 1992.
Rennert et al., International Immunology vol. 9, No. 6, pp. 805-813 (1997).
Riddell et al., Journal of Immunological Methods vol. 128, pp. 189-201, (1990).
Roederer et al., J. Clin. Invest. vol. 99, pp. 1555-1564, 1997.
Rosenberg et al., Science vol. 233, Sep. 1986.
Rosenberg et al., The New England Journal of Medicine pp. 1676-1680, Dec. 22, 1988.
Sansom et al., European Journal of Immunology vol. 23, pp. 295-298, 1993.
Scadden et al., J. Acquired Immune Deficiency Syndrome and Human Retrovirology pp. 523-529, 1997.
Schwartz et al., Cell vol. 71, pp. 1065-1068, Dec. 24, 1992.
Shanafelt et al., The Journal of Immunology vol. 154, pp. 1684-1690, 1995.
Skolnick et al., Trends in Biotech vol. 18, Jan. 2000.
Smithgall et al., Aids Research and Human Retroviruses vol. 11, No. 8, 1995.
Sorge et al., Proceedings of the National Academy of Sciences of the United States of America (Biochemistry) vol. 84, pp. 906-909, Feb. 1987.
Spina et al., The Journal of Clinical Investigation vol. 99, No. 7, pp. 1774-1785, Apr. 1997.
Stassinopoulos et al., Science vol. 272, Jun. 28, 1996.
Tai et al., Journal of Experimental Medicine vol. 184, pp. 753-758, 1996.
Tan et al., Journal of Experimental Medicine vol. 177, No. 1, pp. 165-173, Jan. 1993.
Thompson et al., Proceedings of the National Academy of Sciences vol. 86, pp. 1333-1337, Feb. 1989.
Topalian et al., Journal of Immunological Methods vol. 102, pp. 127-141 (1987).
Turka et al., The Journal of Immunology vol. 144, No. 5, pp. 1646-1653, Mar. 1, 1990.
Van der Pouw-Krann et al. European Journal of Immunology vol. 22, pp. 1237-1241, (1992).
Van der Pouw-Krann et al. European Journal of Immunology vol. 23, pp. 1-5, (1993).
Van Lier et al., European Journal of Immunology vol. 18, pp. 167-172, (1988).
Van Noesel et al., J. Clin. Invest. vol. 86, pp. 293-299 (1990).
Verma et al., Nature vol. 389, pp. 239-242 (1997).
Verwilghen et al., Immunology vol. 72, pp. 269-276 (1991).
Von Fliedner et al., Cellular Immunology vol. 139, pp. 198-207, (1992).
Websters Ninth New Collegiate Dictionary pp. 1132 (1990).
Weir et al., Handbook of Experimental Immunology, vol. 2 (1986), pp. 55.7-55.8.
Weiss et al., Advances in Immunology vol. 41, 1-38, 1987.
Weiss et al., The Journal of Immunology vol. 137, No. 3, pp. 819-825, Aug. 1, 1986.
Williams et al., The Journal of Immunology vol. 135, No. 4, pp. 2249-2255, Oct. 1985.
Wilson et al., Proceedings of the National Academy of Sciences of the United States of America (Genetics) vol. 85, pp. 4421-4425, Jun. 1988.
Yang et al., Journal of Experimental Medicine vol. 168, pp. 1457-1468, Oct. 1988.
Zocchi et al., Cellular Immunology vol. 129, pp. 394-403, 1990.
Zola et al., Immunology and Cell Biology vol. 67, pp. 63-70 (1989).
Linsley et al., "Coexpression and Functional Cooperation of CTLA-4 and CD28 on Activated T Lymphocytes," J. Exp. Med., vol. 176, pp. 1595-1604 (1992).

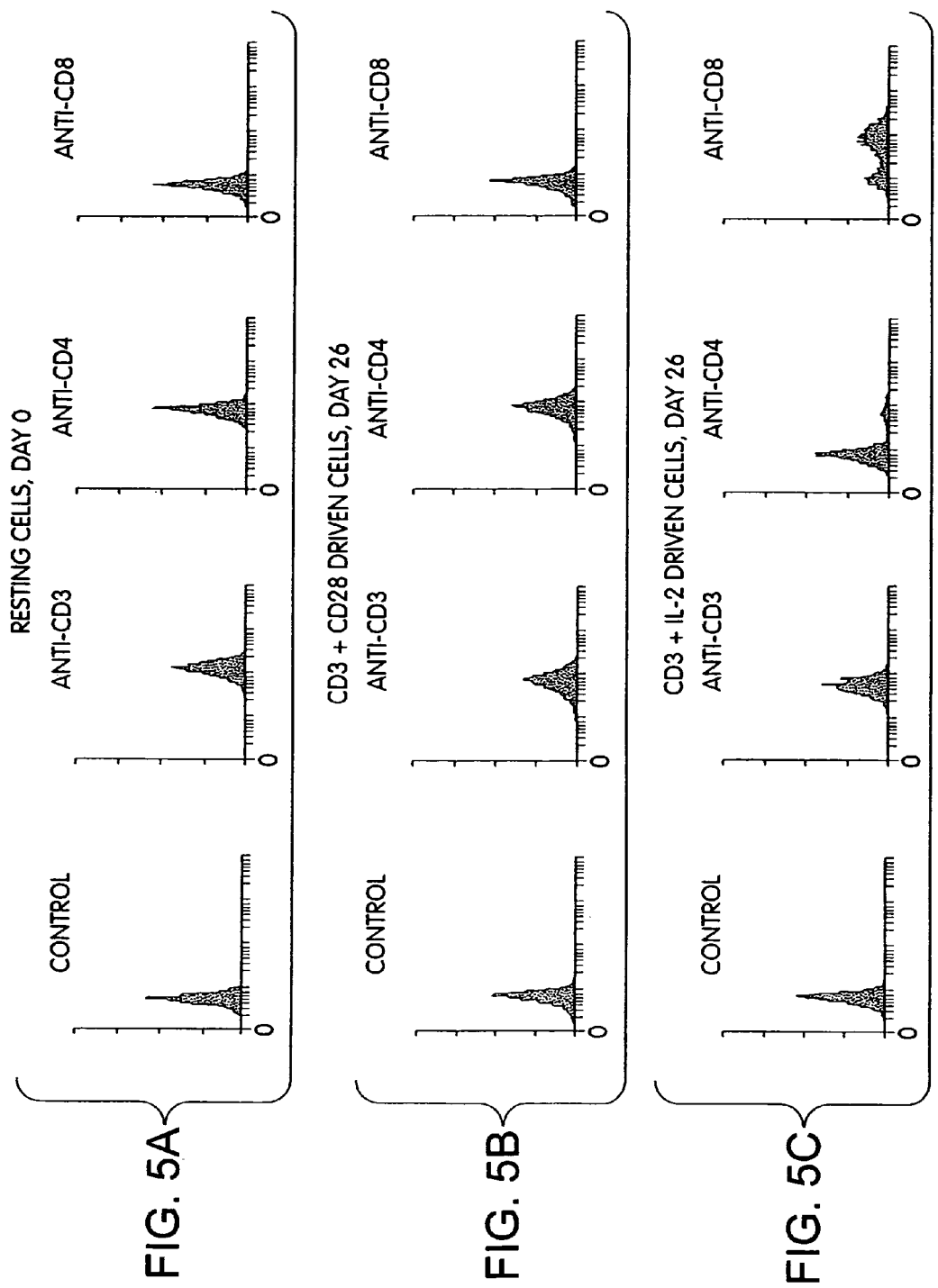

METHODS FOR SELECTIVELY STIMULATING PROLIFERATION OF T CELLS

RELATED APPLICATIONS

This application is a continuation of U.S. application Ser. No. 08/253,964, filed Jun. 3, 1994 (now abandoned). The contents of this application are incorporated herein by reference in their entirety.

BACKGROUND OF THE INVENTION

The development of techniques for propagating T cell populations in vitro has been crucial to many of the recent advances in the understanding of T cell recognition of antigen and T cell activation. The development of culture methods for the generation of human antigen-specific T cell clones has been useful in defining antigens expressed by pathogens and tumors that are recognized by T cells to establish methods of immunotherapy to treat a variety of human diseases. Antigen-specific T cells can be expanded in vitro for use in adoptive cellular immunotherapy in which infusions of such T cells have been shown to have anti-tumor reactivity in a tumor-bearing host. Adoptive immunotherapy has also been used to treat viral infections in immunocompromised individuals.

Techniques for expanding human T cells in vitro have relied on the use of accessory cells and exogenous growth factors, such as IL-2. The use of IL-2 and, for example, an anti-CD3 antibody to stimulate T cell proliferation is known to expand the $CD8^+$ subpopulation of T cells. The requirement for MHC-matched antigen presenting cells as accessory cells presents a significant problem for long-term culture systems. Antigen presenting cells are relatively short lived. Thus, in a long-term culture system, antigen presenting cells must be continuously obtained from a source and replenished. The necessity for a renewable supply of accessory cells is problematic for treatment of immunodeficiencies in which accessory cells are affected. In addition, when treating viral infection, accessory cells which may carry the virus may result in contamination of the entire T cell population during long term culture. An alternative culture method to clone and expand human T cells in vitro in the absence of exogenous growth factor and accessory cells would be of significant benefit.

SUMMARY OF THE INVENTION

This invention pertains to methods for selectively inducing ex vivo expansion of a population of T cells in the absence of exogenous growth factors, such as lymphokines, and accessory cells. In addition, T cell proliferation can be induced without the need for antigen, thus providing an expanded T cell population which is polyclonal with respect to antigen reactivity. The method provides for sustained proliferation of a selected population of $CD4^+$ or $CD8^+$ T cells over an extended period of time to yield a multi-fold increase in the number of these cells relative to the original T cell population.

According to the method of the invention, a population of T cells is induced to proliferate by activating the T cells and stimulating an accessory molecule on the surface of the T cells with a ligand which binds the accessory molecule. Activation of a population of T cells is accomplished by contacting the T cells with a first agent which stimulates a TCR/CD3 complex-associated signal in the T cells. Stimulation of the TCR/CD3 complex-associated signal in a T cell is accomplished either by ligation of the T cell receptor (TCR)/CD3 complex or the CD2 surface protein, or by directly stimulating receptor-coupled signaling pathways. Thus, an anti-CD3 antibody, an anti-CD2 antibody, or a protein kinase C activator in conjunction with a calcium ionophore is used to activate a population of T cells.

To induce proliferation, an activated population of T cells is contacted with a second agent which stimulates an accessory molecule on the surface of the T cells. For example, a population of $CD4^+$ T cells can be stimulated to proliferate with an anti-CD28 antibody directed to the CD28 molecule on the surface of the T cells. Proliferation of a population of $CD8^+$ T cells is accomplished by use of a monoclonal antibody ES5.2D8 which binds to CD9, an accessory molecule having a molecular weight of about 27 kD present on activated T cells. Alternatively, proliferation of an activated population of T cells can be induced by stimulation of one or more intracellular signals which result from ligation of an accessory molecule, such as CD28.

Following activation and stimulation of an accessory molecule on the surface of the T cells, the progress of proliferation of the T cells in response to continuing exposure to the ligand or other agent which acts intracellularly to simulate a pathway mediated by the accessory molecule is monitored. When the rate of T cell proliferation decreases, the T cells are reactivated and restimulated, such as with additional anti-CD3 antibody and a co-stimulatory ligand, to induce further proliferation. In one embodiment, the rate of T cell proliferation is monitored by examining cell size. Alternatively, T cell proliferation is monitored by assaying for expression of cell surface molecules in response to exposure to the ligand or other agent, such as B7-1 or B7-2. The monitoring and restimulation of the T cells can be repeated for sustained proliferation to produce a population of T cells increased in number from about 100- to about 100,000-fold over the original T cell population.

The method of the invention can be used to expand selected T cell populations for use in treating an infectious disease or cancer. The resulting T cell population can be genetically transduced and used for immunotherapy or can be used for in vitro analysis of infectious agents such as HIV. Proliferation of a population of $CD4^+$ cells obtained from an individual infected with HIV can be achieved and the cells rendered resistant to HIV infection. Following expansion of the T cell population to sufficient numbers, the expanded T cells are restored to the individual. Similarly, a population of tumor-infiltrating lymphocytes can be obtained from an individual afflicted with cancer and the T cells stimulated to proliferate to sufficient numbers and restored to the individual. In addition, supernatants from cultures of T cells expanded in accordance with the method of the invention are a rich source of cytokines and can be used to sustain T cells in vivo or ex vivo.

BRIEF DESCRIPTION OF THE DRAWINGS

FIG. 5 depicts fluorescent activated cell sorter analysis (FACS) in which cells were stained after isolation (day 0, panel A), or after 26 days in culture with either CD28 stimulation (panel B) or IL-2 culture (panel C), with phycoerythrin conjugated anti-CD3, CD4, CD8 or with an IgG2a control monoclonal antibody and fluorescence quantified with a flow cytometer.

DETAILED DESCRIPTION OF THE INVENTION

Figure 1:
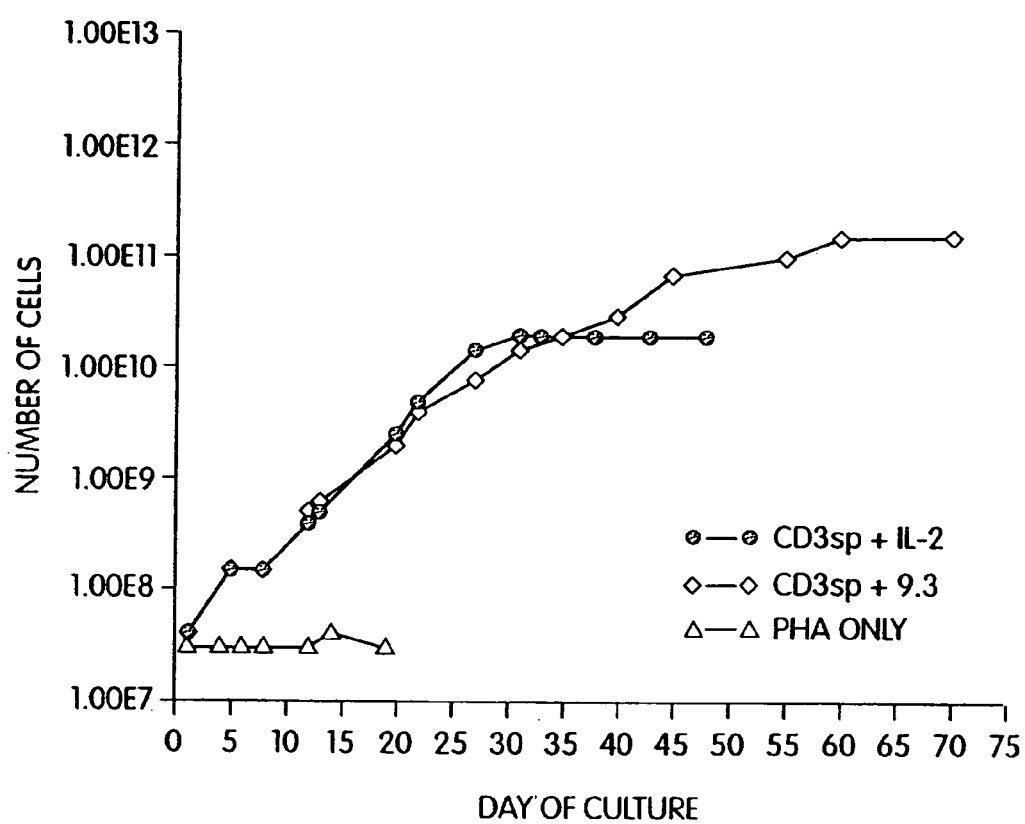
FIG. 1 depicts in vitro growth curves of $CD4^+$ peripheral blood T cells in response to culture with either an anti-CD3 antibody and interleukin-2 (IL-2) (●—●), an anti-CD3 antibody and an anti-CD28 antibody mAb 9.3 (◇—◇) or PHA only (Δ—Δ).

The methods of this invention enable the selective stimulation of a T cell population to proliferate and expand to significant numbers in vitro in the absence of exogenous growth factors or accessory cells. Interaction between the T cell receptor (TCR)/CD3 complex and antigen presented in conjunction with either major histocompatibility complex (MHC) class I or class II molecules on an antigen-presenting cell initiates a series of biochemical events termed antigen-specific T cell activation. The term "T cell activation" is used herein to define a state in which a T cell response has been initiated or activated by a primary signal, such as through the TCR/CD3 complex, but not necessarily due to interaction with a protein antigen. A T cell is activated if it has received a primary signaling event which initiates an immune response by the T cell.

T cell activation can be accomplished by stimulating the T cell TCR/CD3 complex or via stimulation of the CD2 surface protein. An anti-CD3 monoclonal antibody can be used to activate a population of T cells via the TCR/CD3 complex. Although a number of anti-human CD3 monoclonal antibodies are commercially available, OKT3 prepared from hybridoma cells obtained from the American Type Culture Collection or monoclonal antibody G19-4 is preferred. Similarly, binding of an anti-CD2 antibody will activate T cells. Stimulatory forms of anti-CD2 antibodies are known and available. Stimulation through CD2 with anti-CD2 antibodies is typically accomplished using a combination of at least two different anti-CD2 antibodies. Stimulatory combinations of anti-CD2 antibodies which have been described include the following: the T11.3 antibody in combination with the T11.1 or T11.2 antibody (Meuer, S. C. et al. (1984) *Cell* 36:897–906) and the 9.6 antibody (which recognizes the same epitope as T11.1) in combination with the 9-1 antibody (Yang, S. Y. et al. (1986) *J. Immunol.* 137:1097–1100). Other antibodies which bind to the same epitopes as any of the above described antibodies can also be used. Additional antibodies, or combinations of antibodies, can be prepared and identified by standard techniques.

A primary activation signal can also be delivered to a T cell through use of a combination of a protein kinase C (PKC) activator such as a phorbol ester (e.g., phorbol myristate acetate) and a calcium ionophore (e.g., ionomycin which raises cytoplasmic calcium concentrations). The use of these agents bypasses the TCR/CD3 complex but delivers a stimulatory signal to T cells. These agents are also known to exert a synergistic effect on T cells to promote T cell activation and can be used in the absence of antigen to deliver a primary activation signal to T cells.

Although stimulation of the TCR/CD3 complex or CD2 molecule is required for delivery of a primary activation signal in a T cell, a number of molecules on the surface of T cells, termed accessory or costimulatory molecules have been implicated in regulating the transition of a resting T cell to blast transformation, and subsequent proliferation and differentiation. Thus, in addition to the primary activation signal provided through the TCR/CD3 complex, induction of T cell responses requires a second, costimulatory signal. One such costimulatory or accessory molecule, CD28, is believed to initiate or regulate a signal transduction pathway that is distinct from those stimulated by the TCR complex.

Accordingly, to induce an activated population of T cells to proliferate (i.e., a population of T cells that has received a primary activation signal) in the absence of exogenous growth factors or accessory cells, an accessory molecule on the surface of the T cell, such as CD28, is stimulated with a ligand which binds the accessory molecule or with an agent which acts intracellularly to stimulate a signal in the T cell mediated by binding of the accessory molecule. In one embodiment, stimulation of the accessory molecule CD28 is accomplished by contacting an activated population of T cells with a ligand which binds CD28. Activation of the T cells with, for example, an anti-CD3 antibody and stimulation of the CD28 accessory molecule results in selective proliferation of CD4$^+$ T cells. An anti-CD28 monoclonal antibody or fragment thereof capable of crosslinking the CD28 molecule, or a natural ligand for CD28 (e.g., a member of the B7 family of proteins, such as B7-1(CD80) and B7-2 (CD86) (Freedman, A. S. et al. (1987) *J. Immunol.* 137:3260–3267; Freeman, G. J. et al. (1989) *J. Immunol.* 143:2714–2722; Freeman, G. J. et al. (1991) *J. Exp. Med.* 174:625–631; Freeman, G. J. et al. (1993) *Science* 262: 909–911; Azuma, M. et al. (1993) *Nature* 366:76–79; Freeman, G. J. et al. (1993) *J. Exp. Med.* 178:2185–2192)) can be used to induce stimulation of the CD28 molecule. In addition, binding homologues of a natural ligand, whether native or synthesized by chemical or recombinant technique, can also be used in accordance with the invention. Ligands useful for stimulating an accessory molecule can be used in soluble form or immobilized on a solid phase surface as described herein. Anti-CD28 antibodies of fragments thereof useful in stimulating proliferation of CD4$^+$ T cells include monoclonal antibody 9.3, an IgG2a antibody (Dr. Jeffery Ledbetter, Bristol Myers Squibb Corporation, Seattle, Wash.), monoclonal antibody KOLT-2, an IgG1 antibody, 15E8, an IgG1 antibody, 248.23.2, an IgM antibody and EX5.3D10, an IgG2a antibody.

A preferred anti-CD28 antibody is monoclonal antibody 9.3 or EX5.3D10. The EX5.3D10 monoclonal antibody was derived from immunizing a Balb/c mouse with CHO (Chinese hamster ovary) cells transfected with the human CD28 gene (designated CHO-hh). Hybridomas from the fusion were selected by whole cell ELISA screening against Jurkat (human T leukemia) CD28 tranfectants designated Jurkat #7. Reactivity of the EX5.3D10 with CD28 was further confirmed by fluorescent activated cell sorter analysis (FACS) analysis in which it was tested side by side with the monoclonal 9.3 (FIG. 6). Neither antibody bound to untransfected CHO-DG44 cells and their binding profiles were nearly identical for the two CD28 transfectant lines, CHO-hh and Jurkat #7, as well as normal human peripheral blood lymphocytes. A hybridoma which produces the monoclonal antibody EX5.3D10 has been deposited with the American Type Culture Collection, 10801 University Boulevard, Manassas, Va. 20110-2209, on Jun. 4, 1993, at ATCC Deposit No. HB11373.

In another embodiment of the invention, an activated population of CD4$^+$ T cells is stimulated to proliferate by contacting the T cells with an agent which acts intracellularly to stimulate a signal in the T cell mediated by ligation of an accessory molecule, such as CD28. The term "agent", as used herein, is intended to encompass chemicals and other pharmaceutical compounds which stimulate a costimulatory or other signal in a T cell without the requirement for an interaction between a T cell surface receptor and a costimulatory molecule or other ligand. For example, the agent may act intracellularly to stimulate a signal associated with CD28 ligation. In one embodiment, the agent is a non-proteinaceous compound. As the agent used in the method is intended to bypass the natural receptor:ligand stimulatory mechanism, the term agent is not intended to include a cell expressing a natural ligand. Natural ligands for CD28 include members of the B7 family of proteins, such as B7-1(CD80) and B7-2 (CD86).

It is known that CD28 receptor stimulation leads to the production of D-3 phosphoinositides in T cells and that inhibition of the activity of phosphatidylinositol 3-kinase (PI3K) in a T cell can inhibit T cell responses, such as lymphokine production and cellular proliferation. Protein tyrosine phosphorylation has also been shown to occur in T cells upon CD28 ligation and it has been demonstrated that a protein tyrosine kinase inhibitor, herbimycin A, can inhibit CD28-induced IL-2 production (Vandenberghe, P. et al. (1992) *J. Exp. Med.* 175:951–960; Lu, Y. et al. (1992) *J. Immunol.* 149:24–29). Thus, to selectively expand a population of CD4$^+$ T cells, the CD28 receptor mediated pathway can be stimulated by contacting T cells with an activator of PI3K or an agent which stimulates protein tyrosine phosphorylation in the T cell, or both. An activator of PI3K can be identified based upon its ability to stimulate production of at least one D-3 phosphoinositide in a T cell. The term "D-3 phosphoinositide" is intended to include derivatives of phosphatidylinositol that are phosphorylated at the D-3 position of the inositol ring and encompasses the compounds phosphatidylinositol(3)-monophosphate (PtdIns(3)P), phosphatidylinositol(3,4)-bisphosphate (PtdIns(3,4)P$_2$), and phosphatidylinositol(3,4,5)-trisphosphate (PtdIns(3,4,5)P$_3$). Thus, in the presence of a PI3K activator, the amount of a D-3 phosphoinositide in the T cell is increased relative to the amount of the D-3 phosphoinositide in the T cell in the absence of the substance. Production of D-3 phosphoinositides (e.g., PtdIns(3)P, PtdIns(3,4)P$_2$ and/or PtdIns(3,4,5)P$_3$) in a T cell can be assessed by standard methods, such as high pressure liquid chromatography or thin layer chromatography, as discussed above. Similarly, protein tyrosine phosphorylation can be stimulated in a T cell, for example, by contacting the T cell with an activator of protein tyrosine kinases, such as pervanadate (see O'Shea, J. J. et al. (1992) *Proc. Natl. Acad. Sci. USA* 89:10306–103101; and Secrist, J. P. (1993) *J. Biol. Chem.* 268:5886–5893). Alternatively, the T cell can be contacted with an agent which inhibits the activity of a cellular protein tyrosine phosphatase, such as CD45, to increase the net amount of protein tyrosine phosphorylation in the T cell. Any of these agents can be used to expand an activated population of CD4$^+$ T cells in accordance with the methods described herein.

Figure 8:
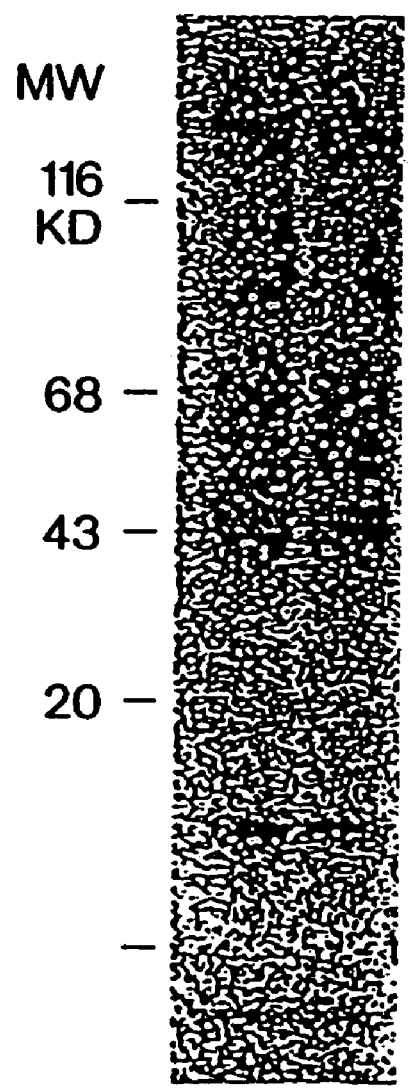
FIG. 8 is a photograph depicting immunoprecipitation analysis of detergent lysates of surface labeled human activated T cells indicating that monoclonal antibody ES5.2D8 reacts with a 27 kD cell surface protein.

In order to induce proliferation and expand a population of CD8$^+$ T cells, an activated population of T cells is stimulated through a 27 kD accessory molecule found on activated T cells and recognized by the monoclonal antibody ES5.2D8. As described in Example 9, a population of CD8$^+$ T cells was preferentially expanded by stimulation with an anti-CD3 monoclonal antibody and the ES5.2D8 monoclonal antibody. The monoclonal antibody ES5.2D8 was produced by immunization of mice with activated human blood lymphocytes and boosted with recombinant human CTLA4 protein produced in E. coli. The ES5.2D8 monoclonal antibody is of the IgG2b isotype and specifically binds to cells transfected with human CTLA4. Hybridomas producing CTLA4-specific antibody were identified by screening by ELISA against human CTLA4 protein as well as by differential FACS against wild type CHO-DG44 cells vs. CHO-105A cells, which are transfected with the human CTLA4 gene. As shown in FIG. 7, the ES5.2D8 clone reacts strongly with both activated human T cells and CHO-105A cells but not with CHO-DCA4 cells, indicating that it does indeed bind to CTLA4. Immunoprecipitation of detergent lysates of surface labeled activated human T cells revealed that ES5.2D8 also reacts with a 27 kD cell surface protein (FIG. 8). A hybridoma which produces the monoclonal antibody ES5.2D8 was deposited on Jun. 4, 1993 with the American Type Culture Collection at ATCC Deposit No. HB11374.

Accordingly, to expand a population of CD8$^+$ T cells, an antibody, such as monoclonal antibody ES5.2D8, or other antibody which recognizes the same 27 kD ligand as ES5.2D8 can be used. As described in Example 10, the epitope recognized by the monoclonal antibody ES5.2D8 was identified by screening a phage display library (PDL). Antibodies which bind to the same epitope as the monoclonal antibody ES5.2D8 are within the scope of the invention. Such antibodies can be produced by immunization with a peptide fragment including the epitope or with the native 27 kD antigen. The term "epitope", as used herein, refers to the actual structural portion of the antigen that is immunologically bound by an antibody combining site. The term is also used interchangeably with "antigenic determinant". A preferred epitope which is bound by an antibody or other ligand which is to be used to stimulate a CD8$^+$ T cell population includes or encompasses, an amino acid sequence:

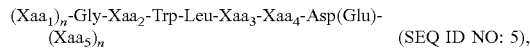
(SEQ ID NO: 5), wherein Xaa$_4$ may or may not be present, Xaa$_1$, Xaa$_2$, Xaa$_3$, Xaa$_4$ and Xaa$_5$ are any amino acid residue and n=0–20, more preferably 0–10, even more preferably 0–5, and most preferably 0–3. In a preferred embodiment, Xaa$_2$ is Cys, Ile or Leu, Xaa$_3$ is Leu or Arg and Xaa$_4$, if present, is Arg, Pro or Phe. As described in Example 10, the monoclonal antibody ES5.2D8, which specifically binds a 27 kD antigen on activated T cells was used to screen a cDNA library from activated T cells to isolate a clone encoding the antigen. Amino acid sequence analysis identified the antigen as CD9(SEQ ID NO: 6). In the native human CD9 molecule, epitope defined by phage display library screening is located at amino acid residues 31–37 (i.e., G L W L R F D (SEQ ID NO: 9)). Accordingly, Xaa$_1$ and Xaa$_4$ are typically additional amino acid residues found at either the amino or carboxy side, or both the amino and carboxy sides, of the core epitope in the human CD9 (the full-length amino acid sequence of which is shown in SEQ ID NO: 6). It will be appreciated by those skilled in the art that in the native protein, additional non-contiguous amino acid residues may also contribute to the conformational epitope recognized by the antibody. Synthetic peptides encompassing the epitope can be created which includes other amino acid residues flanking the core six amino acid residues (i.e., Xaa can alternatively be other amino acid residues than those found in the native CD9 protein). These flanking amino acid residues can function to alter the properties of the resulting peptide, for example to increase the solubility, enhance the immunogenicity or promote dimerization of the resultant peptide. When the peptide is to be used as an immunogen, one or more charged amino acids (e.g., lysine, arginine) can be included to increase the solubility of the peptide and/or enhance the immunogenicity of the peptide. Alternatively, cysteine residues can be included to increase the dimerization of the resulting peptide.

Other embodiments of the invention pertain to expansion of a population of CD8$^+$ T cells by use of an agent which acts intracellularly to stimulate a signal in the T cell mediated by ligation of CD9 or other CD9-associated molecule. It is known that CD9 belongs to the TM4 superfamily of cell surface proteins which span the membrane four times (Boucheix, C. et al. (1990) J. Biol. Chem. 266, 117–122 and Lanza, F. et al. (1990) J. Biol. Chem. 266, 10638–10645). Other members of the TM4 superfamily include CD37, CD53, CD63 and TAPA-1. A role for CD9 in interacting with GTP binding proteins has been suggested (Sechafer, J. G. and Shaw, A. R. E. (1991) Biochem. Biophys. Res. Commun. 179, 401–406). As used herein the term "agent" encompasses chemicals and other pharmaceutical compounds which stimulate a signal in a T cell without the requirement for an interaction between a T cell surface receptor and a ligand. Thus, this agent does not bind to the extracellular portion of CD9, but rather mimics or induces an intracellular signal (e.g., second messenger) associated with ligation of CD9 or a CD9-associated molecule by an appropriate ligand. The ligands described herein (e.g., monoclonal antibody ES5.2D8) can be used to identify an intracellular signal(s) associated with T cell expansion mediated by contact of the CD9 antigen or CD9-associated molecule with an appropriate ligand (as described in the Examples) and examining the resultant intracellular signalling that occurs (e.g., protein tyrosine phosphorylation, calcium influx, activation of serine/threonine and/or tyrosine kinases, phosphatidyl inositol metabolism, etc.). An agent which enhances an intracellular signal associated with CD9 or a CD9-associated molecule can then be used to expand CD8$^+$ T cells. Alternatively, agents (e.g., small molecules, drugs, etc.) can be screened for their ability to inhibit or enhance T cell expansion using a system such as that described in the Examples.

In yet another aspect of the invention, methods for expanding a population of antigen specific T cells are provided. To produce a population of antigen specific T cells, T cells are contacted with an antigen in a form suitable to trigger a primary activation signal in the T cell, i.e., the antigen is presented to the T cell such that a signal is triggered in the T cell through the TCR/CD3 complex. For example, the antigen can be presented to the T cell by an antigen presenting cell in conduction with an MHC molecule. An antigen presenting cell, such as a B cell, macrophage, monocyte, dendritic cell, Langerhan cell, or other cell which can present antigen to a T cell, can be incubated with the T cell in the presence of the antigen (e.g., a soluble antigen) such that the antigen presenting cell presents the antigen to the T cell. Alternatively, a cell expressing an antigen of interest can be incubated with the T cell. For example, a tumor cell expressing tumor-associated antigens can be incubated with a T cell together to induce a tumor-specific response. Similarly, a cell infected with a pathogen, e.g. a virus, which presents antigens of the pathogen can be incubated with a T cell. Following antigen specific activation of a population of T cells, the cells can be expanded in accordance with the methods of the invention. For example, after antigen specificity has been established, T cells can be expanded by culture with an anti-CD3 antibody and an anti-CD28 antibody according to the methods described herein.

The term "antibody" as used herein refers to immunoglobulin molecules and immunologically active portions of immunoglobulin molecules, i.e., molecules that contain an antigen binding site which specifically binds (immunoreacts with) an antigen, such as CD3, CD28. Structurally, the simplest naturally occurring antibody (e.g., IgG) comprises four polypeptide chains, two heavy (H) chains and two light (L) chains inter-connected by disulfide bonds. It has been shown that the antigen-binding function of an antibody can be performed by fragments of a naturally-occurring antibody. Thus, these antigen-binding fragments are also intended to be designated by the term "antibody". Examples of binding fragments encompassed within the term antibody include (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., (1989) Nature 341:544–546) which consists of a VH domain; (v) an isolated complimentarity determining region (CDR); and (vi) an F(ab')$_2$ fragment, a bivalent fragment comprising two Fab fragments linked by a disulfide bridge at the hinge region. Furthermore, although the two domains of the Fv fragment are coded for by separate genes, a synthetic linker can be made that enables them to be made as a single protein chain (known as single chain Fv (scFv); Bird et al. (1988) Science 242:423–426; and Huston et al. (1988) PNAS 85:5879–5883) by recombinant methods. Such single chain antibodies are also encompassed within the term "antibody". Preferred antibody fragments for use in T cell expansion are those which are capable of crosslinking their target antigen, e.g., bivalent fragments such as F(ab')$_2$ fragments. Alternatively, an antibody fragment which does not itself crosslink its target antigen (e.g., a Fab fragment) can be used in conjunction with a secondary antibody which serves to crosslink the antibody fragment, thereby crosslinking the target antigen. Antibodies can be fragmented using conventional techniques as described herein and the fragments screened for utility in the same manner as described for whole antibodies. An antibody of the invention is further intended to include bispecific and chimeric molecules having a desired binding portion (e.g., CD28).

The language "a desired binding specificity for an epitope", as well as the more general language "an antigen binding site which specifically binds (immunoreacts with)", refers to the ability of individual antibodies to specifically immunoreact with a T cell surface molecule, e.g. CD28. That is, it refers to a non-random binding reaction between an antibody molecule and an antigenic determinant of the T cell surface molecule. The desired binding specificity is typically determined from the reference point of the ability of the antibody to differentially bind the T cell surface molecule and an unrelated antigen, and therefore distinguish between two different antigens, particularly where the two antigens have unique epitopes. An antibody which binds specifically to a particular epitope is referred to as a "specific antibody".

"Antibody combining site", as used herein, refers to that structural portion of an antibody molecule comprised of a heavy and light chain variable and hypervariable regions that specifically binds (immunoreacts with) antigen. The term "immunoreact" or "reactive with" in its various forms is used herein to refer to binding between an antigenic determinant-containing molecule and a molecule containing an antibody combining site such as a whole antibody molecule or a portion thereof.

Although soluble forms of antibodies may be used to activate T cells, it is preferred that the anti-CD3 antibody be immobilized on a solid phase surface (e.g., beads). An antibody can be immobilized directly or indirectly by, for example, a secondary antibody, to a solid surface, such as a tissue culture flask or bead. As an illustrative embodiment, the following is a protocol for immobilizing an anti-CD3 antibody on beads. It should be appreciated that the same protocol can be used to immobilize other antibodies or fragments thereof (e.g., an anti-CD28 antibody) to beads.

PROTOCOLS

I. Pre-absorbing Goat Anti-mouse IgG with OKT-3
  A) BioMag Goat anti-Mouse IgG (Advanced Magnetics, Inc., catalog number 8-4340D) is incubated with at least 200 µg of OKT-3 per 5×10$^8$ magnetic particles in PBS for 1 hour at 5° C.
  B) Particles are washed three time in PBS with the aid of a magnetic separation unit.
  Note: Advanced Magnetics also has an anti-Human CD3 directly conjugated (Catalog number 8-4703N) which will induce T-cell stimulation.
II. Pre-labeling Lymphocytes with OKT-3
  A) 1×10$^6$ cells (PBMC) are incubated in PBS with 10 µg/ml of OKT-3 for 15 minutes at room temperature.
  B) Cells are washed twice with PBS.
III. Binding Magnetic Particles to PBMC for Stimulation
  A) PBMC surface labeled with OKT-3 are cultured with Goat anti-Mouse IgG (see above) at one bead per cell following a 30 minute incubation at 20° C. with gentle agitation.
  B) Goat anti-Mouse IgG beads which were previously absorbed to OKT-3 are incubated with PBMC (1:1) for 30 minutes at 20° C. with gentle agitation and cultured.
IV. Binding Magnetic Particles to PBMC for Separation
  Same as above (Part III) except the bead to cell ratio is increased to 20:1 rather than 1:1.

To practice the method of the invention, a source of T cells is obtained from a subject. The term subject is intended to include living organisms in which an immune response can be elicited, e.g., mammals. Examples of subjects include humans, dogs, cats, mice, rats, and transgenic species thereof. T cells can be obtained from a number of sources, including peripheral blood leukocytes, bone marrow, lymph node tissue, spleen tissue, and tumors. Preferably, peripheral blood leukocytes are obtained from an individual by leukopheresis. To isolate T cells from peripheral blood leukocytes, it may be necessary to lyse the red blood cells and separate peripheral blood leukocytes from monocytes by, for example, centrifugation through a PERCOLL™ gradient. A specific subpopulation of T cells, such as CD4$^+$ or CD8$^+$ T cells, can be further isolated by positive or negative selection techniques. For example, negative selection of a T cell population can be accomplished with a combination of antibodies directed to surface markers unique to the cells negatively selected. A preferred method is cell sorting via negative magnetic immunoadherence which utilizes a cocktail of monoclonal antibodies directed to cell surface markers present on the cells negatively selected. For example, to isolate CD4$^+$ cells, a monoclonal antibody cocktail typically includes antibodies to CD14, CD20, CD11b, CD 16, HLA-DR, and CD8. Additional monoclonal antibody cocktails are provided in Table 1.

The process of negative selection results in an essentially homogenous population of CD4+ or CD8+ T cells. The T cells can be activated as described herein, such as by contact with a anti-CD3 antibody immobilized on a solid phase surface or an anti-CD2 antibody, or by contact with a protein kinase C activator (e.g., bryostatin) in conjunction with a calcium ionophore. To stimulate an accessory molecule on the surface of the T cells, a ligand which binds the accessory molecule is employed. For example, a population of CD4+ cells can be contacted with an anti-CD3 antibody and an anti-CD28 antibody, under conditions appropriate for stimulating proliferation of the T cells. Similarly, to stimulate proliferation of CD8+ T cells, an anti-CD3 antibody and the monoclonal antibody ES5.2D8 can be used. Conditions appropriate for T cell culture include an appropriate media (e.g., Minimal Essential Media or RPMI Media 1640) which may contain factors necessary for proliferation and viability, including animal serum (e.g., fetal bovine serum) and antibiotics (e.g., penicillin streptomycin). The T cells are maintained under conditions necessary to support growth, for example an appropriate temperature (e.g., 37° C.) and atmosphere (e.g., air plus 5% $CO_2$).

To maintain long term stimulation of a population of T cells following the initial activation and stimulation, it is necessary to separate the T cells from the activating stimulus (e.g., the anti-CD3 antibody) after a period of exposure. The T cells are maintained in contact with the co-stimulatory ligand throughout the culture term. The rate of T cell proliferation is monitored periodically (e.g., daily) by, for example, examining the size or measuring the volume of the T cells, such as with a Coulter Counter. A resting T cell has a mean diameter of about 6.8 microns. Following the initial activation and stimulation and in the presence of the stimulating ligand, the T cell mean diameter will increase to over 12 microns by day 4 and begin to decrease by about day 6. When the mean T cell diameter decreases to approximately 8 microns, the T cells are reactivated and restimulated to induce further proliferation of the T cells. Alternatively, the rate of T cell proliferation and time for T cell restimulation can be monitored by assaying for the presence of cell surface molecules, such as B7-1, B7-2, which are induced on activated T cells. As described in Example 5, it was determined that CD4+ T cells do not initially express the B7-1 receptor, and that with culture, expression is induced. Further, the B7-1 expression was found to be transient, and could be re-induced with repeated anti-CD3 restimulation. Accordingly, cyclic changes in B7-1 expression can be used as a means of monitoring T cell proliferation; where decreases in the level of B7-1 expression, relative to the level of expression following an initial or previous stimulation or the level of expression in an unstimulated cell, indicates the time for restimulation.

For inducing long term stimulation of a population of CD4+ or CD8+ T cells, it may be necessary to reactivate and restimulate the T cells with a anti-CD3 antibody and an anti-CD28 antibody or monoclonal antibody ES5.2D8 several times to produce a population of CD4+ or CD8+ cells increased in number from about 10- to about 1,000-fold the original T cell population. Using this methodology, it is possible to get increases in a T cell population of from about 100- to about 100,000-fold an original resting T cell population. Moreover, as described in Example 6, T cells expanded by the method of the invention secrete high levels of cytokines (e.g., IL-2, IFNγ, IL-4, GM-CSF and TNFα) into the culture supernatants. For example, as compared to stimulation with IL-2, CD4+ T cells expanded by use of anti-CD3 and anti-CD28 costimulation secrete high levels of GM-CSF and TNFα into the culture medium. These cytokines can be purified from the culture supernatants or the supernatants can be used directly for maintaining cells in culture. Similarly, the T cells expanded by the method of the invention together with the culture supernatant and cytokines can be administered to support the growth of cells in vivo. For example, in patients with tumors, T cells can be obtained from the individual, expanded in vitro and the resulting T cell population and supernatant, including cytokines such as TNFα, can be readministered to the patient to augment T cell growth in vivo.

Although the antibodies used in the methods described herein can be readily obtained from public sources, such as the ATCC, antibodies to T cell surface accessory molecules, the CD3 complex, or CD2 can be produced by standard techniques. Methodologies for generating antibodies for use in the methods of the invention are described in further detail below.

I. Antibody Production

A. The Immunogen. The term "immunogen" is used herein to describe a composition containing a peptide or protein as an active ingredient used for the preparation of antibodies against an antigen (e.g., CD3, CD28). When a peptide or protein is used to induce antibodies it is to be understood that the peptide can be used alone, or linked to a carrier as a conjugate, or as a peptide polymer.

To generate suitable antibodies, the immunogen should contain an effective, immunogenic amount of a peptide or protein, optionally as a conjugate linked to a carrier. The effective amount of peptide per unit dose depends, among other things, on the species of animal inoculated, the body weight of the animal and the chosen immunization regimen as is well known in the art. The immunogen preparation will typically contain peptide concentrations of about 10 micrograms to about 500 milligrams per immunization dose, preferably about 50 micrograms to about 50 milligrams per dose. An immunization preparation can also include an adjuvant as part of the diluent. Adjuvants such as complete Freund's adjuvant (CFA), incomplete Freund's adjuvant (IFA) and alum are materials well known in the art, and are available commercially from several sources.

Those skilled in the art will appreciate that, instead of using natural occurring forms of the antigen (e.g., CD3, CD28) for immunization, synthetic peptides can alternatively be employed towards which antibodies can be raised for use in this invention. Both soluble and membrane bound forms of the protein or peptide fragments are suitable for use as an immunogen and can also be isolated by immunoaffinity purification as well. A purified form of protein, such as may be isolated as described above or as known in the art, can itself be directly used as an immunogen, or alternatively, can be linked to a suitable carrier protein by conventional techniques, including by chemical coupling means as well as by genetic engineering using a cloned gene of the protein. The purified protein can also be covalently or noncovalently modified with non-proteinaceous materials such as lipids or carbohydrates to enhance immunogenecity or solubility. Alternatively, a purified protein can be coupled with or incorporated into a viral particle, a replicating virus, or other microorganism in order to enhance immunogenicity. The protein may be, for example, chemically attached to the viral particle or microorganism or an immunogenic portion thereof.

In an illustrative embodiment, a purified CD28 protein, or a peptide fragment thereof (e.g., produced by limited proteolysis or recombinant DNA techniques) is conjugated to a carrier which is immunogenic in animals. Preferred carriers include proteins such as albumins, serum proteins (e.g., globulins and lipoproteins), and polyamino acids. Examples of useful proteins include bovine serum albumin, rabbit serum albumin, thyroglobulin, keyhole limpet hemocyanin, egg ovalbumin and bovine gamma-globulins. Synthetic polyamino acids such as polylysine or polyarginine are also useful carriers. With respect to the covalent attachment of CD28 protein or peptide fragments to a suitable immunogenic carrier, there are a number of chemical cross-linking agents that are known to those skilled in the art. Preferred cross-linking agents are heterobifunctional cross-linkers, which can be used to link proteins in a stepwise manner. A wide variety of heterobifunctional cross-linkers are known in the art, including succinimidyl 4-(N-maleimidomethyl) cyclohexane-1-carboxylate (SMCC), m-Maleimidobenzoyl-N-hydroxysuccinimide ester (MBS); N-succinimidyl (4-iodoacetyl) aminobenzoate (SIAB), succinimidyl 4-(p-maleimidophenyl) butyrate (SMPB), 1-ethyl-3-(3-dimethylaminopropyl) carbodiimide hydrochloride (EDC); 4-succinimidyloxycarbonyl-a-methyl-a-(2-pyridyldithio)-tolune (SMPT), N-succinimidyl 3-(2-pyridyldithio) propionate (SPDP), succinimidyl 6-[3-(2-pyridyldithio) propionate] hexanoate (LC-SPDP).

In may also be desirable to simply immunize an animal with whole cells which express a protein of interest (e.g., CD28) on their surface. Various cell lines can be used as immunogens to generate monoclonal antibodies to an antigen, including, but not limited to T cells. For example, peripheral blood T cells can be obtained from a subject which constituitively express CD28, but can be activated in vitro with anti-CD3 antibodies, PHA or PMA. Alternatively, an antigen specific (e.g., alloreactive) T cell clone can be activated to express CD28 by presentation of antigen, together with a costimulatory signal, to the T cell. Whole cells that can be used as immunogens to produce CD28 specific antibodies also include recombinant transfectants. For example, COS and CHO cells can be reconstituted by transfection with a CD28 cDNA to produce cells expressing CD28 on their surface. These transfectant cells can then be used as immunogens to produce anti-CD28 antibodies. Other examples of transfectant cells are known, particularly eukaryotic cells able to glycosylate the CD28 protein, but any procedure that works to express transfected CD28 genes on the cell surface could be used to produce the whole cell immunogen.

Alternative to a CD28-expressing cell or an isolated CD28 protein, peptide fragments of CD28 or other surface antigen such as CD9 can be used as immunogens to generate antibodies. For example, the CD9 epitope bound by the ES5.2D8 monoclonal antibody comprises an amino acid sequence: $(Xaa_1)_n$-Gly-$Xaa_2$-Trp-Leu-$Xaa_3$-$Xaa_4$-Asp(Glu)-$(Xaa_5)_n$ (SEQ ID NO: 5), wherein $Xaa_4$ may or may not be present, $Xaa_1$, $Xaa_2$, $Xaa_3$, $Xaa_4$ and $Xaa_5$ are any amino acid residue and n=0–20, more preferably 0–10, even more preferably 0–5, and most preferably 0–3. In a preferred embodiment, $Xaa_2$ is Cys, Ile or Leu, $Xaa_3$ is Leu or Arg and $Xaa_4$, if present, is Arg, Pro or Phe. Thus, a peptide having the amino acid sequence of SEQ ID NO: 5 can be used as an immunogen. Accordingly, the invention further encompasses an isolated CD9 peptide comprising an amino acid sequence: $(Xaa_1)_n$-Gly-$Xaa_2$-Trp-Leu-$Xaa_3$-$Xaa_4$-Asp(Glu)-$(Xaa_5)_n$ (SEQ ID NO: 5), wherein $Xaa_4$ may or may not be present, $Xaa_1$, $Xaa_2$, $Xaa_3$, $Xaa_4$ and $Xaa_5$ are any amino acid residue and n=0–20, more preferably 0–10, even more preferably 0–5, and most preferably 0–3. In a preferred embodiment, $Xaa_2$ is Cys, Ile or Leu, $Xaa_3$ is Leu or Arg and $Xaa_4$, if present, is Arg, Pro or Phe. Alternatively, it has been found that the ES5.2D8 monoclonal antibody cross-reacts with a number of other peptide sequences (determined by phage display technology as described in Example 3). Examples of these other peptide sequences are shown below:

```
2D8#2     (SEQ ID NO: 1)       HQFCDHWGCWLLRETHIFTP

2D8#4     (SEQ ID NO: 2)       HQFCDHWGCWLLRETHIFTP

2D8#10    (SEQ ID NO: 3)       HQFCDHWGCWLLRETHIFTP

2D8#6     (SEQ ID NO: 4)       LRLVLEDPGIWLRPDYFFPA

GCWLLRE   (phage 2D8#2, 4, 10; SEQ ID NO: 7)

GIWLRPD   (phage 2D8#6;        SEQ ID NO: 8)

GLWLRFD   (CD9 sequence;       SEQ ID NO: 9)
```

Any of these peptides, or other peptides containing a stretch of seven amino acids bracketed in bold type (representing the epitope bound by the antibody) possibly flanked by alternative amino acid residues, can also be used as immunogens to produce an antibody for use in the methods of the invention and are encompassed by the invention. For use as immunogens, peptides can be modified to increase solubility and/or enhance immunogenicity as described above.

B. Polyclonal Antibodies. Polycolonal antibodies to a purified protein or peptide fragment thereof can generally be raised in animals by multiple subcutaneous (sc) or intraperitoneal (ip) injections of an appropriate immunogen, such as the extracellular domain of the protein, and an adjuvant. A polyclonal antisera can be produced, for example, as described in Lindsten, T. et al. (1993) *J. Immunol.* 151: 3489–3499. In an illustrative embodiment, animals are typically immunized against the immunogenic protein, peptide or derivative by combining about 1 μg to 1 mg of protein with Freund's complete adjuvant and injecting the solution intradermally at multiple sites. One month later the animals are boosted with ⅕ to ¹⁄₁₀ the original amount of immunogen in Freund's complete adjuvant (or other suitable adjuvant) by subcutaneous injection at multiple sites. Seven to 14 days later, the animals are bled and the serum is assayed for anti-protein or peptide titer (e.g., by ELISA). Animals are boosted until the titer plateaus. Also, aggregating agents such as alum can be used to enhance the immune response.

Such mammalian-produced populations of antibody molecules are referred to as "polyclonal" because the population comprises antibodies with differing immunospecificities and affinities for the antigen. The antibody molecules are then collected from the mammal (e.g., from the blood) and isolated by well known techniques, such as protein A chromatography, to obtain the IgG fraction. To enhance the specificity of the antibody, the antibodies may be purified by immunoaffinity chromatography using solid phase-affixed immunogen. The antibody is-contacted with the solid phase-affixed immunogen for a period of time sufficient for the immunogen to immunoreact with the antibody molecules to form a solid phase-affixed immunocomplex. The bound antibodies are separated from the complex by standard techniques.

C. Monoclonal Antibodies. The term "monoclonal antibody" or "monoclonal antibody composition", as used herein, refers to a population of antibody molecules that contain only one species of an antigen binding site capable of immunoreacting with a particular epitope of an antigen.

A monoclonal antibody composition thus typically displays a single binding affinity for a particular protein with which it immunoreacts. Preferably, the monoclonal antibody used in the subject method is further characterized as immunoreacting with a protein derived from humans.

Monoclonal antibodies useful in the methods of the invention are directed to an epitope of an antigen(s) on T cells, such that complex formation between the antibody and the antigen (also referred to herein as ligation) induces stimulation and T cell expansion. A monoclonal antibody to an epitope of an antigen (e.g., CD3, CD28) can be prepared by using a technique which provides for the production of antibody molecules by continuous cell lines in culture. These include but are not limited to the hybridoma technique originally described by Kohler and Milstein (1975, *Nature* 256:495–497), and the more recent human B cell hybridoma technique (Kozbor et al. (1983) *Immunol Today* 4:72), EBV-hybridoma technique (Cole et al. (1985), *Monoclonal Antibodies and Cancer Therapy,* Alan R. Liss, Inc., pp. 77–96), and trioma techniques. Other methods which can effectively yield monoclonal antibodies useful in the present invention include phage display techniques (Marks et al. (1992) *J Biol Chem* 16007–16010).

In one embodiment, the antibody preparation applied in the subject method is a monoclonal antibody produced by a hybridoma cell line. Hybridoma fusion techniques were first introduced by Kohler and Milstein (Kohler et al. *Nature* (1975) 256:495–97; Brown et al. (1981) *J. Immunol* 127: 539–46; Brown et al. (1980) *J Biol Chem* 255:4980–83; Yeh et al. (1976) *PNAS* 76:2927–31; and Yeh et al. (1982) *Int. J. Cancer* 29:269–75). Thus, the monoclonal antibody compositions of the present invention can be produced by the following method, which comprises the steps of:

(a) Immunizing an animal with a protein (e.g., CD28) or peptide thereof. The immunization is typically accomplished by administering the immunogen to an immunologically competent mammal in an immunologically effective amount, i.e., an amount sufficient to produce an immune response. Preferably, the mammal is a rodent such as a rabbit, rat or mouse. The mammal is then maintained for a time period sufficient for the mammal to produce cells secreting antibody molecules that immunoreact with the immunogen. Such immunoreaction is detected by screening the antibody molecules so produced for immunoreactivity with a preparation of the immunogen protein. Optionally, it may be desired to screen the antibody molecules with a preparation of the protein in the form in which it is to be detected by the antibody molecules in an assay, e.g., a membrane-associated form of the antigen (e.g., CD28). These screening methods are well known to those of skill in the art, e.g., enzyme-linked immunosorbent assay (ELISA) and/or flow cytometry.

(b) A suspension of antibody-producing cells removed from each immunized mammal secreting the desired antibody is then prepared. After a sufficient time, the mouse is sacrificed and somatic antibody-producing lymphocytes are obtained. Antibody-producing cells may be derived from the lymph nodes, spleens and peripheral blood of primed animals. Spleen cells are preferred, and can be mechanically separated into individual cells in a physiologically tolerable medium using methods well known in the art. Mouse lymphocytes give a higher percentage of stable fusions with the mouse myelomas described below. Rat, rabbit and frog somatic cells can also be used. The spleen cell chromosomes encoding desired immunoglobulins are immortalized by fusing the spleen cells with myeloma cells, generally in the presence of a fusing agent such as polyethylene glycol (PEG). Any of a number of myeloma cell lines may be used as a fusion partner according to standard techniques; for example, the P3-NS1/1-Ag4-1, P3-x63-Ag8.653 or Sp2/O-Ag14 myeloma lines. These myeloma lines are available from the American Type Culture Collection (ATCC), Rockville, Md.

The resulting cells, which include the desired hybridomas, are then grown in a selective medium, such as HAT medium, in which unfused parental myeloma or lymphocyte cells eventually die. Only the hybridoma cells survive and can be grown under limiting dilution conditions to obtain isolated clones. The supernatants of the hybridomas are screened for the presence of antibody of the desired specificity, e.g., by immunoassay techniques using the antigen that has been used for immunization. Positive clones can then be subcloned under limiting dilution conditions and the monoclonal antibody produced can be isolated. Various conventional methods exist for isolation and purification of the monoclonal antibodies so as to free them from other proteins and other contaminants. Commonly used methods for purifying monoclonal antibodies include ammonium sulfate precipitation, ion exchange chromatography, and affinity chromatography (see, e.g., Zola et al. in *Monoclonal Hybridoma Antibodies: Techniques And Applications,* Hurell (ed.) pp. 51–52 (CRC Press 1982)). Hybridomas produced according to these methods can be propagated in vitro or in vivo (in ascites fluid) using techniques known in the art.

Generally, the individual cell line may be propagated in vitro, for example in laboratory culture vessels, and the culture medium containing high concentrations of a single specific monoclonal antibody can be harvested by decantation, filtration or centrifugation. Alternatively, the yield of monoclonal antibody can be enhanced by injecting a sample of the hybridoma into a histocompatible animal of the type used to provide the somatic and myeloma cells for the original fusion. Tumors secreting the specific monoclonal antibody produced by the fused cell hybrid develop in the injected animal. The body fluids of the animal, such as ascites fluid or serum, provide monoclonal antibodies in high concentrations. When human hybridomas or EBV-hybridomas are used, it is necessary to avoid rejection of the xenograft injected into animals such as mice. Immunodeficient or nude mice may be used or the hybridoma may be passaged first into irradiated nude mice as a solid subcutaneous tumor, cultured in vitro and then injected intraperitoneally into pristane primed, irradiated nude mice which develop ascites tumors secreting large amounts of specific human monoclonal antibodies.

Media and animals useful for the preparation of these compositions are both well known in the art and commercially available and include synthetic culture media, inbred mice and the like. An exemplary synthetic medium is Dulbecco's minimal essential medium (DMEM; Dulbecco et al. (1959) *Virol.* 8:396) supplemented with 4.5 gm/l glucose, 20 mM glutamine, and 20% fetal caf serum. An exemplary inbred mouse strain is the Balb/c.

D. Combinatorial Antibodies. Monoclonal antibody compositions of the invention can also be produced by other methods well known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies (for descriptions of combinatorial antibody display see e.g., Sastry et al. (1989) *PNAS* 86:5728; Huse et al. (1989) *Science* 246:1275; and Orlandi et al. (1989) *PNAS* 86:3833). After immunizing an animal with an appropriate immunogen (e.g., CD3, CD28) as described above, the antibody repertoire of the resulting B-cell pool is cloned. Methods are generally known for directly obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies (Larrick et al. (1991) *Biotechniques* 11:152–156). A similar strategy can also been used to amplify human heavy and light chain variable regions from human antibodies (Larrick et al. (1991) *Methods: Companion to Methods in Enzymology* 2:106–110).

In an illustrative embodiment, RNA is isolated from activated B cells of, for example, peripheral blood cells, bone marrow, or spleen preparations, using standard protocols (e.g., U.S. Pat. No. 4,683,202; Orlandi, et al. *PNAS* (1989) 86:3833–3837; Sastry et al., *PNAS* (1989) 86:5728–5732; and Huse et al. (1989) *Science* 246:1275–1281.) First-strand cDNA is synthesized using primers specific for the constant region of the heavy chain(s) and each of the κ and λ light chains, as well as primers for the signal sequence. Using variable region PCR primers, the variable regions of both heavy and light chains are amplified, each alone or in combination, and ligated into appropriate vectors for further manipulation in generating the display packages. Oligonucleotide primers useful in amplification protocols may be unique or degenerate or incorporate inosine at degenerate positions. Restriction endonuclease recognition sequences may also be incorporated into the primers to allow for the cloning of the amplified fragment into a vector in a predetermined reading frame for expression.

The V-gene library cloned from the immunization-derived antibody repertoire can be expressed by a population of display packages, preferably derived from filamentous phage, to form an antibody display library. Ideally, the display package comprises a system that allows the sampling of very large variegated antibody display libraries, rapid sorting after each affinity separation round, and easy isolation of the antibody gene from purified display packages. In addition to commercially available kits for generating phage display libraries (e.g., the Pharmacia *Recombinant Phage Antibody System*, catalog no. 27-9400-01; and the Stratagene SurfZAP™ phage display kit, catalog no. 240612), examples of methods and reagents particularly amenable for use in generating a variegated antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffths et al. (1993) *EMBO J* 2:725–734; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; and Barbas et al. (1991) *PNAS* 88:7978–7982.

In certain embodiments, the V region domains of heavy and light chains can be expressed on the same polypeptide, joined by a flexible linker to form a single-chain Fv fragment, and the scFV gene subsequently cloned into the desired expression vector or phage genome. As generally described in McCafferty et al., *Nature* (1990) 348:552–554, complete $V_H$ and $V_L$ domains of an antibody, joined by a flexible $(Gly_4-Ser)_3$ linker can be used to produce a single chain antibody which can render the display package separable based on antigen affinity. Isolated scFV antibodies immunoreactive with the antigen can subsequently be formulated into a pharmaceutical preparation for use in the subject method.

Once displayed on the surface of a display package (e.g., filamentous phage), the antibody library is screened with the protein, or peptide fragment thereof, to identify and isolate packages that express an antibody having specificity for the protein. Nucleic acid encoding the selected antibody can be recovered from the display package (e.g., from the phage genome) and subcloned into other expression vectors by standard recombinant DNA techniques.

E. Hybridomas and Methods of Preparation. Hybridomas useful in the present invention are those characterized as having the capacity to produce a monoclonal antibody which will specifically immunoreact with an antigen of interest (e.g., CD3, CD28). Methods for generating hybridomas that produce, e.g., secrete, antibody molecules having a desired immunospecificity, e.g., having the ability to immunoreact with the CD28 antigen, and/or an identifiable epitope of CD28 are well known in the art. Particularly applicable is the hybridoma technology described by Niman et al. (1983) *PNAS* 80:4949–4953; and by Galfre et al. (1981) *Meth. Enzymol.* 73:3–46.

II. Uses of the Methods of the Invention

The method of this invention can be used to selectively expand a population of $CD4^+$ or $CD8^+$ T cells for use in the treatment of infectious disease, cancer and immunotherapy. As a result of the method described herein, a population of T cells which is polyclonal with respect to antigen reactivity, but essentially homogeneous with respect to either $CD4^+$ or $CD8^+$ can be produced. In addition, the method allows for the expansion of a population of T cells in numbers sufficient to reconstitute an individual's total $CD4^+$ or $CD8^+$ T cell population (the population of lymphocytes in an individual is approximately $10^{11}$). The resulting T cell population can be genetically transduced and used for immunotherapy or can be used in methods of in vitro analyses of infectious agents. For example, a population of tumor-infiltrating lymphocytes can be obtained from an individual afflicted with cancer and the T cells stimulated to proliferate to sufficient numbers. The resulting T cell population can be genetically transduced to express tumor necrosis factor (TNF) or other factor and restored to the individual.

One particular use for the $CD4^+$ T cells expanded by the method of the invention is in the treatment of HIV infection in an individual. Prolonged infection with HIV eventually results in a marked decline in the number of $CD4^+$ T lymphocytes. This decline, in turn, causes a profound state of immunodeficiency, rendering the patient susceptible to an array of life threatening opportunistic infections. Replenishing the number of $CD4^+$ T cells to normal levels may be expected to restore immune function to a significant degree.

Thus, the method described herein provides a means for selectively expanding CD4$^+$ T cells to sufficient numbers to reconstitute this population in an HIV infected patient. It may also be necessary is to avoid infecting the T cells during long-term stimulation or it may desirable to render the T cells permanently resistant to HIV infection. There are a number of techniques by which T cells may be rendered either resistant to HIV infection or incapable of producing virus prior to restoring the T cells to the infected individual. For example, one or more anti-retroviral agents can be cultured with CD4$^+$ T cells prior to expansion to inhibit HIV replication or viral production (e.g., drugs that target reverse transcriptase and/or other components of the viral machinery, see e.g., Chow et al. (1993) *Nature* 361, 650–653).

Several methods can be used to genetically transduce T cells to produce molecules which inhibit HIV infection or replication. For example, in one embodiment, T cells can be genetically transduced to produce transdominant inhibitors, which are mutated, nonfunctional forms of normal HIV gene products. Transdominant inhibitors function to oligomerize or compete for binding with the wild type HIV proteins. Several transdominant inhibitors have been derived from HIV proteins including tat, rev, and gag. The function of tat is to enhance the transcription of viral genes by binding to the trans activation response element (tar) found in the promoter region of most HIV genes. Rev, through binding to the rev response element (RRE) found at the 5' end of unspliced HIV transcripts, facilitates the transport of unprocessed mRNA from the nucleus to the cytoplasm for packaging into virions. Gag is first synthesized as a single polypeptide and subsequently cleaved by a virus-encoded protease to yield three structural proteins, p15, p17, and p24. Transdominant inhibitors derived from these gene products have been demonstrated to inhibit infection of cells cultured with lab pet HIV isolates. One example of a transdominant inhibitor which appears to act by forming nonfunctional multimers with wild-type Rev is RevM10. RevM10 construct has blocked infection of CEM cells by HTLV-IIIB for up to 28 days (Malim et al. *JEM* 176:1197, Bevec et al. *PNAS* 89:9870). In these studies, RevM10 failed to demonstrate adverse effect on normal T cell function as judged by the criteria of growth rate and IL-2 secretion.

In another approach T cells can be transduced to produce molecules known as "molecular decoys" which are binding elements for viral proteins critical to replication or assembly, such as TAR. High level retrovirus-mediated expression of TAR in CEM SS cells has been found to effectively block the ARV-2 HIV isolate, as measured by RT assay (Sullenger et al. *Cell* 63:601). Importantly, it also blocked SIV (SIV-mac251) infection, suggesting that inhibition of HIV infection with molecular decoys may be generally applicable to various isolates and thereby alleviate the problem of hypervariability. Further, it has been demonstrated that TAR expression has no discernible effects on cell viability (Sullenger et al. *J. Virol.* 65:6811). Another "molecular decoy" which T cells can be transduced to produce is a soluble CD4 tagged at the carboxy terminus with a KDEL (lysine-aspartic acid-glutamic acid-leucine) sequence, a signal for ER retention (Buonocore and Rose, *PNAS* 90:2695)(*Nature* 345:625). The sCD4-KDEL gene expression is driven by the HIV LTR. H9 cells transduced with the sCD4-KDEL construct show up regulation of expression of intracellular CD4 upon HIV infection. This strategy effectively blocked production of HIV MN for up to 60 days post infection. The proposed advantage of this inhibitor is that the virus should not be able to escape it's effect by mutating because CD4 binding is essential for HIV infectivity.

T cells can also be transduced to express antisense molecules and ribozyme which block viral replication or infection. Viral replication can be inhibited with a variety of antisense strategies. One particular ribozyme which cleaves HIV integrase (Sioud and Drlica, *PNAS* 88:7303), has been developed and may offer an approach to blocking infection as opposed to merely viral production.

Another approach to block HIV infection involves transducing T cells with HIV-regulated toxins. Two examples of this type of approach are the diphtheria toxin A gene (Harrison et al. *AIDS Res. Hum. Retro.* 8:39) and the herpes simplex virus type 1 thymidine kinase gene (HSV TK) (Caruso and Klatzmann, *PNAS* 89:182). In both cases, transcription was under the control of HIV regulatory sequences. While the diphtheria toxin is itself toxic, the HSV TK requires the addition of acyclovir to kill infected cells. For example the use of HSV TK followed by the addition of 10 μm acyclovir for 17 days totally blocks HIV infection of HUT 78 cells for up to 55 days of culture.

The methods for stimulating and expanding a population of antigen specific T cells are useful in therapeutic situations where it is desirable to upregulate an immune response (e.g., induce a response or enhance an existing response) upon administration of the T cells to a subject. For example, the method can be used to enhance a T cell response against tumor-associated antigens. Tumor cells from a subject typically express tumor-associated antigens but may be unable to stimulate a costimulatory signal in T cells (e.g., because they lacks expression of costimulatory molecules). Thus, tumor cells can be contacted with T cells from the subject in vitro and antigen specific T cells expanded according to the method of the invention and the T cells returned to the subject. Alternatively, T cells can be stimulated and expanded as described herein to induce or enhance responsiveness to pathogenic agents, such as viruses (e.g., human immunodeficiency virus), bacteria, parasites and fungi.

This invention is further illustrated by the following examples which should not be construed as limiting. The contents of all references and published patent applications cited throughout this application are hereby incorporated by reference. The following methodology described in the Materials and Methods section was used throughout the examples set forth below.

Methods and Materials

Preparation of Immobilized Anti-CD3 Antibody

Tissue culture flasks were coated with anti-CD3 monoclonal antibody. Although a number of anti-human CD3 monoclonal antibodies are available, OKT3 prepared from hybridoma cells obtained from the American Type Culture Collection was used in this procedure. For any anti-CD3 antibody the optimal concentration to be coated on tissue cultured flasks must be determined experimentally. With OKT3, the optimal concentration was determined to be typically in the range of 0.1 to 10 micrograms per milliliter. To make coating solution, the antibody was suspended in 0.05 M tris-HCl, pH 9.0 (Sigma Chemical Co., St. Louis, Mo.). Coating solution sufficient to cover the bottom of a tissue culture flask was added (Falcon, Nunc or Costar) and incubated overnight at 4° C. The flasks were washed three times with phosphate buffered saline without calcium or magnesium (PBS w/o Ca or Mg) and blocking buffer (PBS w/o Ca or Mg plus 5% bovine serum albumin) added to cover the bottom of the flask and were incubated two hours at room temperature. After this incubation, flasks were used directly or frozen for storage, leaving the blocking solution on the flask.

Isolation of Peripheral Blood Leukocytes (PBLs)

Samples were obtained by leukopheresis of healthy donors. Using sterile conditions, the leukocytes were transferred to a T800 culture flask. The bag was washed with Hanks balanced salt solution w/o calcium or magnesium (HBSS w/o) (Whittaker Bioproducts, Inc., Walkersville, Md.). The cells were diluted with HBSS w/o and mixed well. The cells were then split equally between two 200 milliliter conical-bottom sterile plastic tissue culture tubes. Each tube was brought up to 200 ml with HBSS w/o and spun at 1800 RPM for 12 minutes in a Beckman TJ-6 centrifuge. The supernatant was aspirated and each pellet resuspended in 50 ml HBSS w/o. The cells were transferred to two 50 ml conical-bottom tubes and spun at 1500 RPM for eight minutes. Again the supernatant was aspirated.

To lyse the red blood cells, the cell pellets were resuspended in 50 ml of ACK lysing buffer (Biofluids, Inc., Rockville Md., Catalog #304) at room temperature with gentle mixing for three minutes. The cells were again pelleted by spinning at 1500 RPM for 8 minutes. After aspirating the supernatant, the pellets were combined into one 50 ml tube in 32 ml HBSS w/o.

Separation of the PBLs from monocytes was accomplished by centrifugation through a PERCOLL™ gradient. To prepare 1 liter of PERCOLL™ solution (PERCOLL™-MO), 716 ml of PERCOLL™ (Pharmacia, Piscataway, N.J., Catalog #17-0891-01) was combined with 100 ml 1.5 M sodium chloride, 20 ml 1M sodium-HEPES, and 164 ml water. All reagents must be tissue culture grade and sterile filtered. After mixing, this solution was filtered through a sterile 0.2 µm³ filter and stored at 4° C. 24 ml of PERCOLL™-MO was added to each of two 50 ml conical bottom tubes. To each tube 16 ml of the cell suspension was added. The solution was mixed well by gently inverting the tubes. The tubes were spun at 2800 RPM for 30 minutes without a brake. The tubes were removed from the centrifuge, being careful not to mix the layers. The PBLs were at the bottoms of the tubes. Then, the supernatant was aspirated and the PBLs were washed in HBSS w/o by centrifuging for 8 minutes at 1500 RPM.

Cell Sorting Via Negative Magnetic Immunoadherence

The cell sorting via negative magnetic immunoadherence must be performed at 4° C. The washed cell pellets obtained from the PERCOLL™ gradients described above were resuspended in coating medium (RPMI-1640 (Biowittaker, Walkersville, Md., Catalog #12-167Y), 3% fetal calf serum (FCS) (or 1% human AB⁻ serum or 0.5% bovine serum albumin) 5 mM EDTA (Quality Biological, Inc., Gaithersburg, Md., Catalog #14-117-1), 2 mM L-glutamine (BioWhittaker, Walkersville, Md., Catalog #17-905C), 20 mM HEPES (Biowhittaker, Walkersville, Md., Catalog #17-757A), 50 µg/ml gentamicin (BioWhittaker, Walkersville, Md., Catalog #17-905C)) to a cell density of $20 \times 10^6$ per ml. A cocktail of monoclonal antibodies directed to cell surface markers was added to a final concentration of 1 µg/ml for each antibody. The composition of this cocktail is designed to enrich for either CD4⁺ or CD28⁺ T cells. Thus, the cocktail will typically include antibodies to CD14, CD20, CD11b, CD16, HLA-DR, and (for CD4⁺ cells only) CD8. (See Table 1 for a list of sorting monoclonal antibody cocktails.) The tube containing cells and antibodies was rotated at 4° C. for 30–45 minutes. At the end of this incubation, the cells were washed three times with coating medium to remove unbound antibody. Magnetic beads coated with goat anti-mouse IgG (Dynabeads M-450, Catalog #11006, P&S Biochemicals, Gaithersburg, Md.) and prewashed with coating medium were added at a ratio of three beads per cell. The cells and beads were then rotated for 1–1.5 hours at 4° C. The antibody-coated cells were removed using a magnetic particle concentrator according to the manufacturer's directions (MPC-1, Catalog #12001, P&S Biochemicals, Gaithersburg, Md.). The nonadherent cells were washed out of the coating medium and resuspended in an appropriate culture medium.

TABLE 1

Sorting Monoclonal Antibody Cocktails:
(Italicized mAbs are available from the ATCC)

| Cocktail | Targets | Representative mAbs |
|---|---|---|
| rt-A | CD14 | *63D3 (IgG1), 20.3 (IgM)* |
|  | CD20 | 1F5 (IgG2$_a$), Leu-16 (IgG1) |
|  | CD16 | FC-2.2 (IgG2$_b$), *3G8 (IgG1)* |
|  | HLA-DR | *2.06 (IgG1)*, HB10a (IgG) |
| rT-B | CD14 | *63D3 (IgG1), 20.3 (IgM)* |
|  | CD21 | *HB5 (IgG2$_a$)* |
|  | CD16 | FC-2.2 (IgG2$_b$), *3G8 (IgG1)* |
|  | HLA-DR | *2.06 (IgG1)*, HB10a (IgG) |
| r9.3-A | CD14 | *63D3 (IgG1), 20.3 (IgM)* |
|  | CD20 | 1F5 (IgG2$_a$), Leu-16 (IgG1) |
|  | CD11b | *OKMI (IgG2$_b$)*, 60.1 (IgG2$_b$) |
|  | CD16 | FC-2.2 (IgG2$_b$), 3G8 *(IgG1)* |
|  | HLA-DR | *2.06 (IgG1)*, HB10a (IgG) |
| r9.3-B | CD14 | *63D3 (IgG1), 20.3 (IgM)* |
|  | CD21 | *HB5 (IgG2$_a$)* |
|  | CD11b | *OKMI (IgG2$_b$)*, 60.1 (IgG2$_b$) |
|  | CD16 | FC-2.2 (IgG2$_b$), 3G8 *(IgG1)* |
|  | HLA-DR | *2.06 (IgG1)*, HB10a (IgG) |
| rCD4-A | CD14 | *63D3 (IgG1), 20.3 (IGM)* |
|  | CD20 | IF5 (IgG2$_a$), Leu-16 (IGg1) |
|  | CD11b | *OKMI (IgG2$_b$)*, 60.1 (IgG2$_b$) |
|  | CD16 | FC-2.2 (IgG$_b$), 3G8 *(IgG1)* |
|  | HLA-DR | *2.06 (IgG1)*, HB10a (IgG) |
|  | CD8 | *51.1(IgG2)*, *G10-1.1(IgG2$_a$)*, *OKT8, (IgG2$_a$)* |
| rCD8-B | CD14 | *63D3 (IgG1), 20.3 (IgM)* |
|  | CD20 | IF5 (IgG2$_a$), Leu-16 (IGg1) |
|  | CD11b | *OKMI (IgG2$_b$)*, 60.1 (IgG2$_b$) |
|  | CD16 | FC-2.2 (IgG2$_b$), 3G8 *(IgG1)* |
|  | HLA-DR | *2.06 (IgG1)*, HB10a (IgG) |
|  | CD4 | G17-2.8 (IgG1) |
| rM0 | CD2 | 35.1 (IgG2$_a$), 9.6 (IgG2$_a$) |
|  | CD20 | IF5 (IgG2$_a$), Leu-16 (IGg1) |
| rB | CD2 | 35.1 (IgG2$_a$), 9.6 (IgG2$_a$) |
|  | CD14 | *63D3 (IgG1), 20.3 (IgM)* |
|  | CD11b | *OKMI (IgG2$_b$)*, 60.1 (IgG2$_b$) |
|  | CD16 | FC-2.2 (IgG2$_b$), 3G8 *(IgG1)* |

Long Term Stimulation

Tissue culture flasks precoated with anti-CD3 monoclonal antibody were thawed and washed three times with PBS. The purified T cells were added at a density of $2 \times 10^6$/ml. Anti-CD28 monoclonal antibody mAb 9.3 (Dr. Jeffery Ledbetter, Bristol Myers Squibb Corporation, Seattle, Wash.) or EX5.3D10, ATCC Deposit No. HB11373 (Repligen Corporation, Cambridge, Mass.) was added at a concentration of 1 µg/ml and cells were cultured at 37° C. overnight. The cells were then detached from the flask by forceful pipetting and transferred to a fresh untreated flask at a density of $0.5 \times 10^6$/ml. Thereafter, the cells were resuspended every other day by forceful pipetting and diluted to $0.5 \times 10^6$/ml. The mean diameter of the cells was monitored daily with a Coulter Counter 2M interfaced to a Coulter Channelyzer. Resting T cells have a mean diameter of 6.8 microns. With this stimulation protocol, the mean diameter increased to over 12 microns by day 4 and then began to decrease by about day 6. When the mean diameter decreased to about 8 microns, the cells were again stimulated overnight with anti-CD3 and anti-CD28 as above. It was important that the cells not be allowed to return to resting diameter. This cycle was repeated for as long as three months. It can be expected that the time between restimulations will progressively decrease.

EXAMPLE 1

Long Term Growth of CD4+ T cells with Anti-CD3 and Anti-CD28 Antibodies

Previous known methods to culture T cells in vitro require the addition of exogenous feeder cells or cellular growth factors (such as interleukin 2 or 4) and a source of antigen or mitogenic plant lectin. Peripheral blood CD28+ T cells were isolated by negative selection using magnetic immunobeads and monoclonal antibodies as described in the Methods and Materials section above. CD4+ cells were further isolated from the T cell population by treating the cells with anti-CD8 monoclonal antibody and removing the CD8+ cells with magnetic immunobeads. Briefly, T cells were obtained from leukopheresis of a normal donor, and purified with FICOLL™ density gradient centrifugation, followed by magnetic immunobead sorting. The resulting CD28+, CD4+ T cells were cultured in defined medium (X-Vivo10 containing gentamicin and L-glutamine (Whittaker Bioproducts) at an initial density of $2.0 \times 10^6$/ml by adding cells to culture dishes containing plastic-adsorbed Goat anti-mouse IgG (Kirkegaard and Perry Laboratories, Gaithersburg, Md.) and anti-CD3 mAb G19-4. After 48 hours, the cells were removed and placed in flasks containing either hIL-2 (5%, CalBiochem) or anti-CD28 mAb (500 ng/ml). The cells cultured with IL-2 were fed with fresh IL-2 at 2-day intervals. Fresh medium was added to all cultures as required to maintain a cell density of $0.5 \times 10^6$/ml. Cells were restimulated at approximately weekly intervals by culture on plastic-adsorbed anti-CD3 mAb for 24 hours, the cells removed and placed at $1.0 \times 10^6$/ml in fresh medium in flasks containing either IL-2 or anti-CD28 mAb.

In the example shown in FIG. 1, the culture vessel initially contained $50 \times 10^6$ cells, and the cells were cultured in an optimal amount of mitogenic lectin PHA, or cultured with cyclic stimulation of plastic immobilized anti-CD3 mAb in the presence of interleukin 2 or anti-CD28 mAb 9.3. The cells cultured in PHA alone did not proliferate, with all cells dying by about day 20 of culture, demonstrating the functional absence of accessory cells. In contrast, the cells grown in anti-CD3 with IL-2 or anti-CD28 entered a logarithmic growth phase, with equal rates of growth for the first three weeks of culture. However, the anti-CD3 cultures began to diverge in growth rates during the fourth week of culture, with the IL-2 fed cells entering a plateau phase after a $\sim 2.8 \log_{10}$ expansion. In contrast, the cultures grown in the presence of anti-CD28 remained in logarithmic growth until the sixth week of culture, at which time there had been a $\sim 3.8 \log_{10}$ expansion. Thus, CD28 receptor stimulation, perhaps by anti-CD28 crosslinking, is able to stimulate the growth of CD4+ T cells in the absence of fetal calf serum or accessory cells, and furthermore, about 10-fold more cells can be obtained using anti-CD28 as opposed to addition of exogenous IL-2. In repeated experiments, CD4+ T cell expansion using anti-CD28 antibody consistently yielded more CD4+ T cells than expansion using IL-2 (e.g., up to 1000-fold more cells). This system has the added advantage of not requiring the presence of accessory cells which may be advantageous in clinical situations where accessory cells are limiting or defective.

EXAMPLE 2

Long Term Growth of Anti-CD28-Treated T cells in Medium Containing Fetal Calf Serum Another series of experiments tested whether the growth advantage of CD28 receptor stimulation was due to replacement of factors normally present in fetal calf serum. T cells were obtained from leukopheresis of a normal donor, and purified with FICOLL™ density gradient centrifugations, followed by magnetic immunobead sorting. The resulting CD28+, CD4+ T cells were cultured at an initial density of $2.0 \times 10^6$/ml in medium (RPMI-1640 containing 10% heat-inactivated fetal calf serum [Hyclone, Logan, Utah] and gentamicin and L-glutamine) by adding cells to culture dishes containing plastic-adsorbed OKT3. After 48 hours, the cells were removed and placed in flasks containing either hIL-2 (10% final concentration, CalBiochem) or anti-CD28 mAb 9.3 (800 ng/ml). The cells were fed with fresh medium as required to maintain a cell density of $0.5 \times 10^6$/ml, and restimulated at approximately weekly intervals by culture on plastic adsorbed anti-CD3 mAb for 24 hours.

Figure 2:
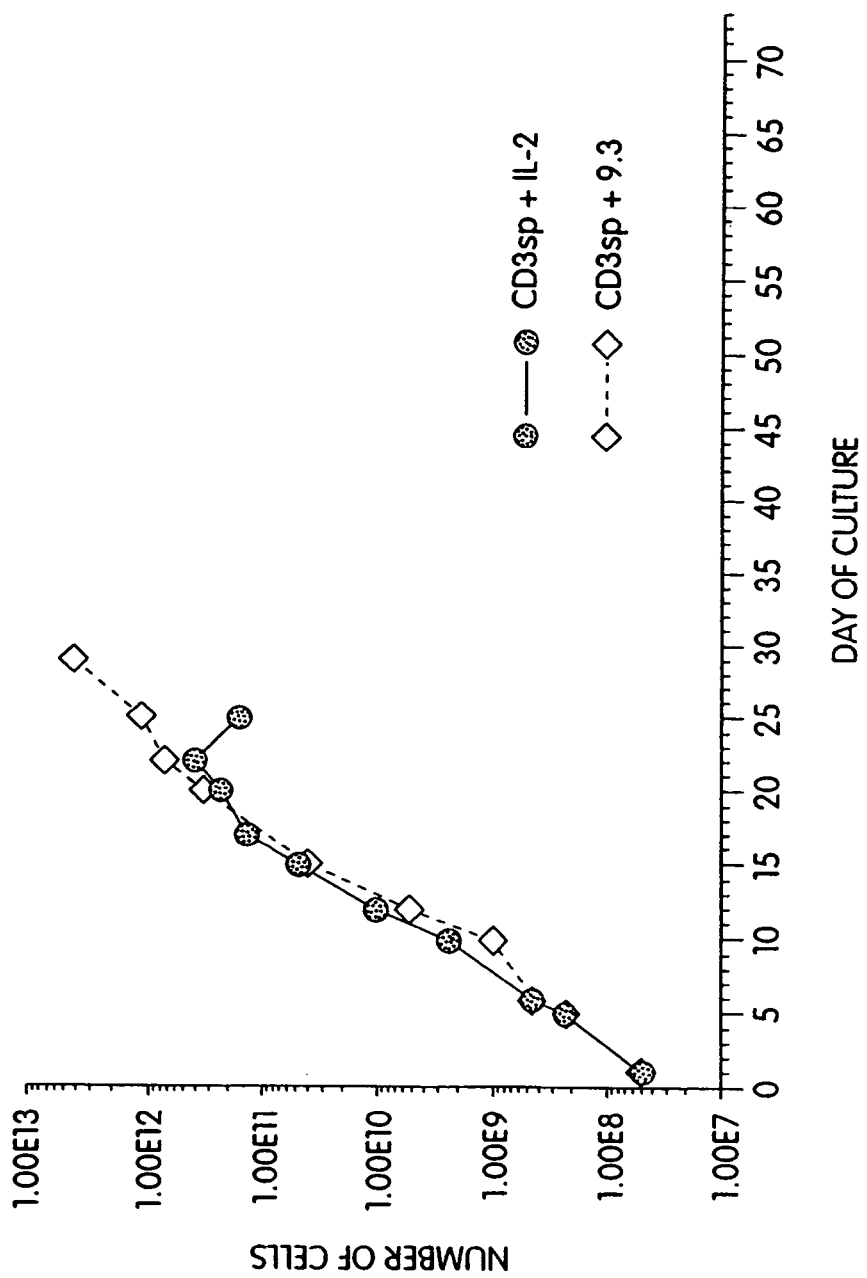
FIG. 2 depicts the growth curve of $CD4^+$ peripheral blood T cells cultured in fetal calf serum and either anti-CD3 antibodies and IL-2 (●—●) or an anti-CD3 antibody and an anti-CD28 antibody, mAb 9.3 (◇—◇).

As shown in FIG. 2, the cells entered logarithmic growth phase, with equal rates of growth for the first three weeks of culture. However, the anti-CD3 cultures began to diverge in growth rates during the fourth week of culture, with the IL-2 fed cells entering a plateau phase after a $\sim 4.0 \log_{10}$ expansion. In contrast, the cultures grown in the presence of anti-CD28 remained in logarithmic growth until the fifth week of culture, at which time there had been a $\sim 5.1 \log_{10}$ expansion. Thus, CD28 stimulation resulted in a $\sim 125,000$-fold expansion of the initial culture while IL-2 feeding resulted in a 10,000-fold expansion of cells.

EXAMPLE 3

Long Term Growth of T cells in Phorbol Ester, Ionomycin and Anti-CD28-Stimulated T cells Further experiments tested whether alternative methods of activating T cells would also permit CD28 stimulated growth. Pharmacologic activation of T cells with PMA and ionomycin is thought to mimic antigen receptor triggering of T cells via the TCR/CD3 complex. T cells were obtained from leukopheresis of a normal donor, and purified with sequential FICOLL™ and PERCOLL™ density gradient centrifugations, followed by magnetic immunobead sorting. The resulting CD28+, CD4+ T cells were cultured at an initial density of $2.0 \times 10^6$/ml by adding cells to culture dishes containing phorbol myristic acid (PMA 3 ng/ml, Sigma) and ionomycin (120 ng/ml, Calbiochem, lot #3710232). After 24 hours, the cells were diluted to $0.5 \times 10^6$/ml and placed in flasks containing either rIL-2 (50 IU/ml, Boerhinger Mannheim, lot #11844900)) or anti-CD28 mAb (1 ug/ml). The cells were fed with fresh medium as required to maintain a cell density of $0.5 \times 10^6$/ml, and restimulated cyclically at approximately weekly intervals by readdition of PMA and ionomycin. Fresh IL-2 was added to the IL-2 containing culture at daily intervals.

Figure 3:
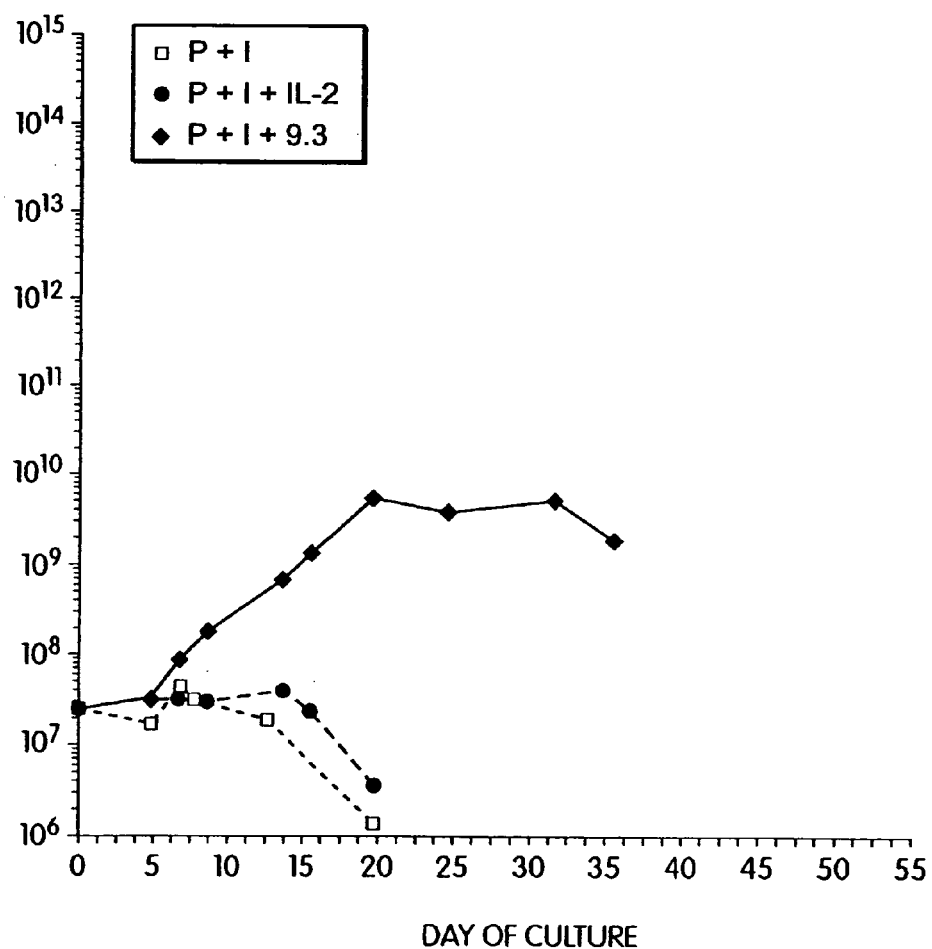
FIG. 3 depicts the growth curves of CD4+ peripheral blood T cells cultured in the presence of phorbol myristic acid (PMA) and ionomycin with or without IL-2, or with an anti-CD28 antibody, mAb 9.3. The symbols are as follows: PMA and ionomycin (P+I) is represented by (□); PMA, ionomycin and IL-2 (P+I+IL-2) is represented by (●); and PMA, ionomycin and anti-CD28 antibody (P+I+9.3) is represented by (♦).

The results of this experiment are shown in FIG. 3. T cells that were purified of accessory cells did not grow in cell numbers in the presence of PMA ("P" in the Figure) and ionomycin ("I" in the Figure), with or without IL-2. The cells clumped and enlarged, as indicated by size analysis, indicating the cells had been induced to enter the G1 phase of the cell cycle but did not progress to DNA synthesis and cell division. In contrast, addition of CD28 mAb to PMA plus ionomycin treated cells resulted in logarithmic cell growth. Thus, anti-CD3 mAb is not required to provide T cell activation. It should be appreciated that other activators of protein kinase C, such as bryostatin or diacylglycerol can be used in place of PMA.

EXAMPLE 4

Figure 4:
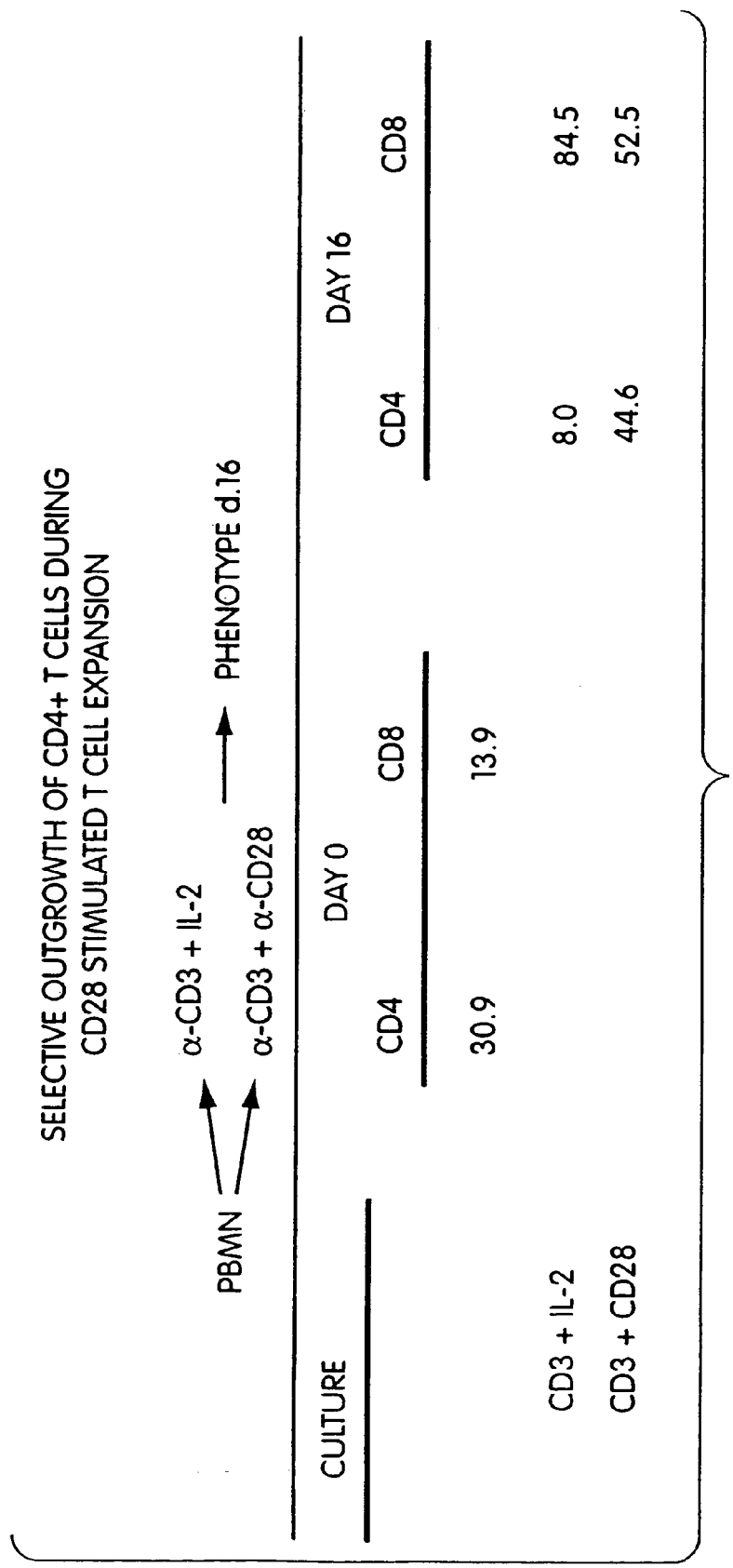
FIG. 4 is a schematic representation of the selective expansion of CD4+ T cells following CD28 stimulation in comparison to T cell stimulation with IL-2.
Figure 6A:
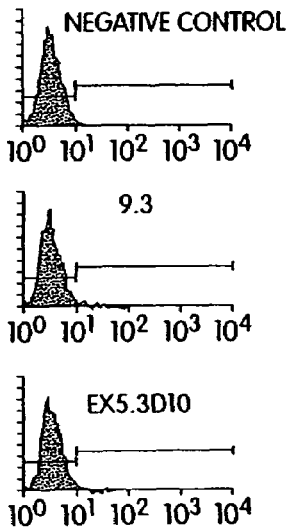
FIG. 6 shows FACS analysis of the EX5.3D10 monoclonal antibody depicting reactivity with CD28 in comparison to an anti-CD28 monoclonal antibody 9.3. The following cell lines were tested: Panel A, untransfected CHO-DG44 cells; Panel B, CHO-HH cells; Panel C, unactivated peripheral blood lymphocytes; and Panel D, Jurkat No. 7 cells.
Figure 6B:
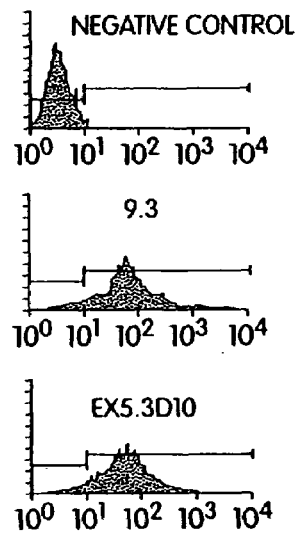
Figure 6C:
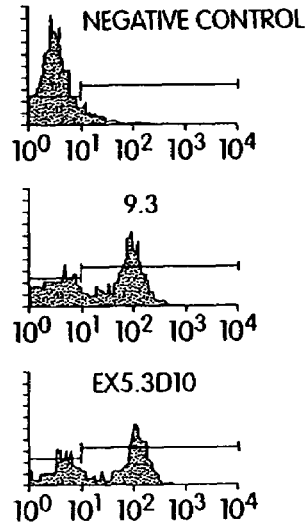
Figure 6D:
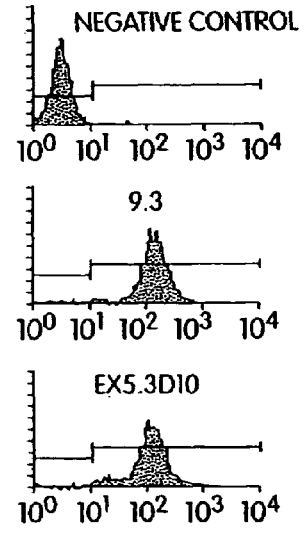
Figure 7A:
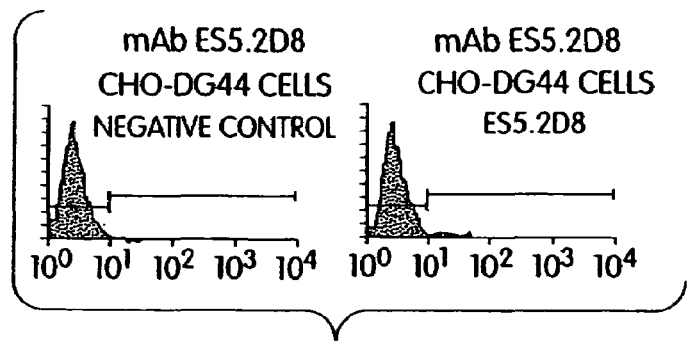
FIG. 7 shows FACS analysis of the ES5.2D8 monoclonal antibody depicting the binding reactivity with the following cell lines: Panel A, CHO-DG44 cells; Panel B, CHO-105A cells; Panel C, unactivated human peripheral blood lymphocytes; and Panel D, PMA activated peripheral blood lymphocytes.
Figure 7B:
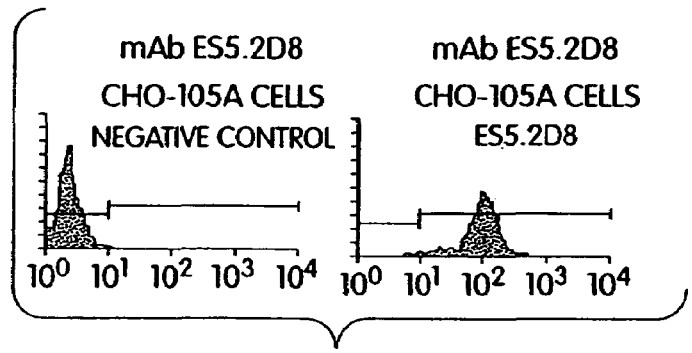
Figure 7C:
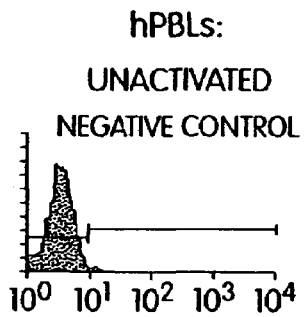
Figure 7D:
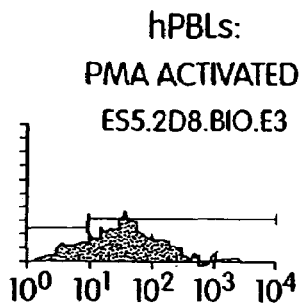

Immunophenotype of Cells Cultured with Anti-CD3 Stimulation and Addition of IL2 or Anti-CD28 mAb To examine the subsets of T cells that are expanded, PBL were propagated for 16 days using either anti-CD3 and IL-2 or anti-CD3 and anti-CD28. FIG. 4 demonstrates the selective enrichment of CD4 cells from peripheral blood lymphocytes. Mononuclear cells were isolated from blood by ficoll hypaque density gradient centrifugation. The cells were stained with CD4 and CD8 monoclonal antibodies, and analyzed for the percent positive cells on day 0. The cells were then cultured on plastic immobilized anti-CD3 monoclonal antibody G19-4 plus IL-2 or plastic immobilized anti-CD3 monoclonal antibody G19-4 plus anti-CD28 monoclonal antibody 9.3 (0.5 µg/ml). The cells were isolated from culture on day 16, and repeat staining for CD4 and CD8 antigens was done by flow cytometry. Data was gated on the lymphocyte population by forward angle light scatter and side scatter. By this analysis, the % CD4 and CD8 cells were 8.0% and 84.5% in the cells grown in IL-2, and 44.6% and 52.5% in the cells grown in CD28. These results suggest that CD28 expansion favors the $CD4^+$ cell, in contrast to the well-established observation that $CD8^+$ cells predominate in cells grown in IL-2 (for example, see D. A. Cantrell and K. A. Smith, (1983), *J. Exp. Med* 158:1895 and Gullberg, M. and K. A. Smith (1986) *J. Exp. Med.* 163, 270).

To further test this possibility, $CD4^+$ T cells were enriched to 98% purity using negative selection with monoclonal antibodies and magnetic immunobeads as described above. Fluorescent Activated Cell Sorter (FACS) Analysis was used to examine the phenotype of the T cells cultured with anti-CD3 and anti-CD28. Cells were pelleted by centrifugation and resuspended in PBS/1% BSA. The cells were then washed by repeating this procedure twice. The cells were pelleted and resuspended in 100 µl of primary antibody solution, vortexed, and kept on ice for one hour. After washing twice in PBS/1% BSA, the cells were resuspended in 100 µl of fluorescein-labeled goat-anti-mouse IgG and incubated for 30 minutes on ice. At the end of this incubation, the cells were washed twice in PBS and resuspended in 500 µl 1% paraformaldehyde in PBS. The labeled cells were analyzed on an Ortho Cytofluorograph. Cells were stained after isolation, or after 26 days in culture, with phycoerythrin conjugated anti-CD3 (Leu-4), CD4 (Leu-3A), CD8 (OKT8) or with IgG2a control monoclonal antibodies and fluorescence quantified with a flow cytometer. The cells were cultured for one month using anti-CD3 and either IL-2 or anti-CD28 to propagate the cells. There was equal expansion of the cells for the first 26 days of the culture (not shown), however, as can be seen in FIG. 5, the phenotype of the cells diverged progressively with increasing time in culture so that at day 26 of culture, the predominant cell in anti-CD28 culture was $CD4^+$ while the cells in the IL-2 culture were predominantly $CD8^+$. Thus, CD28 receptor stimulation, perhaps by crosslinking, is able to selectively expand T cells of the CD4 phenotype while the conventional method of in vitro T cell culture yields cells of the CD8 phenotype. Additional experiments have been conducted with similar results, indicating that CD28 stimulation of initially mixed populations of cells is able to yield cultures containing predominately or exclusively CD4 T cells, and thus one can expand and "rescue" the CD4 cells that were initially present in limiting amounts.

EXAMPLE 5

Figure 9:
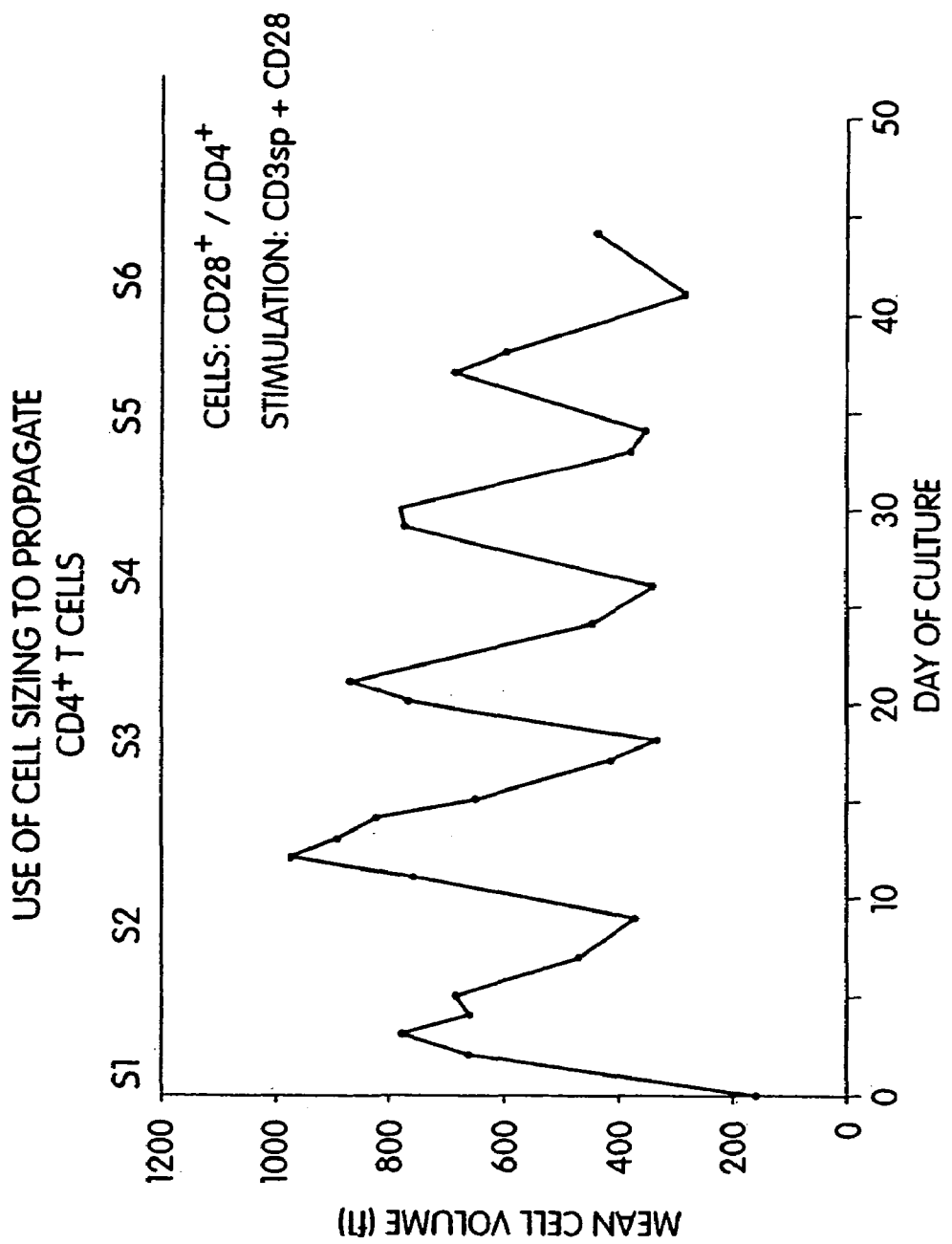
FIG. 9 depicts the increases in mean cell volume of CD4+ T cells following stimulation (S1, S2, S3, S4, S5 and S6) with an anti-CD3 monoclonal antibody and an anti-CD28 monoclonal antibody over days in culture.

Use of Cell Sizing or Cyclic Expression of B7 on CD4+ T cells to Monitor T Cell Expansion To determine the time of T cell restimulation, changes in cell volume were monitored using a Coulter Counter ZM interfaced with a Coulter. $CD28^+$, $CD4^+$ T cells were isolated as described by magnetic immunoselection, and cultured in the presence of anti-CD28 mAb 9.3 (0.5 µg/ml) and restimulated with plastic immobilized anti-CD3 monoclonal antibody G19-4 as indicted. FIG. 9 demonstrates the cyclic changes in cell volume during six consecutive restimulations ("S1" to "S6") performed essentially as described in Example 1. Briefly, cells were expanded with anti-CD3 and anti-CD28 over three weeks in culture. Cells were changed to fresh medium at each restimulation with anti-CD3 antibody. Stimulations were spaced at ten day intervals. The cells were restimulated whenever cell volume decreased to <400 fl.

Figure 10:
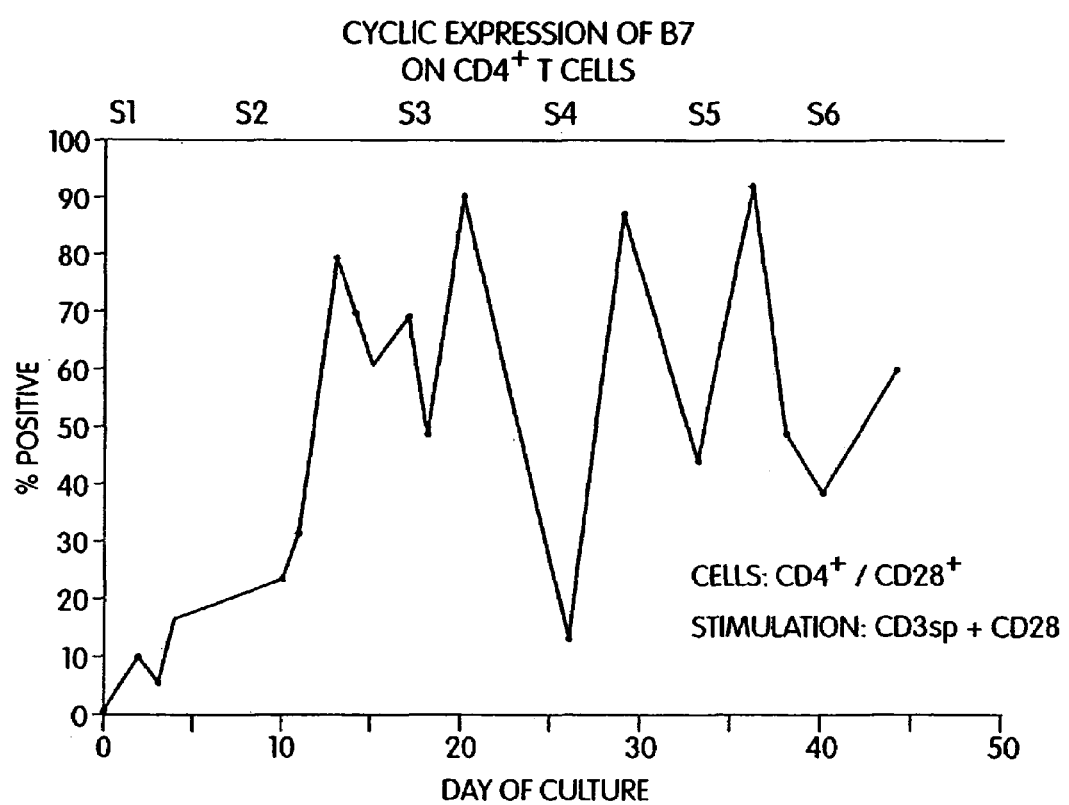
FIG. 10 depicts the cyclic expression of B7-1 on CD4+ T cells following stimulation (S1, S2, S3, S4, S5 and S6) with an anti-CD3 monoclonal antibody and an anti-CD28 monoclonal antibody over days in culture.

In another experiment, cyclic expression of the B7-1 antigen was used to determine the time for T cell restimulation. The cells obtained from the experiment shown in FIG. 10 were stained with a CTLA-4Ig fusion protein (obtained from Repligen Corporation; see also Linsley P. S. et al. (1991) *J. Exp. Med.* 174, 561–569) and analyzed by flow cytometry to measure B7-1 receptor expression. It was determined that $CD4^+$ T cells do not initially express the B7-1 receptor, and that with culture, expression is induced. Further, the B7-1 expression was found to be transient, and to be re-induced with repeated anti-CD3 restimulation.

EXAMPLE 6

Production of Cytokines by T Cells Following Anti-CD28 Stimulation

Figure 11:
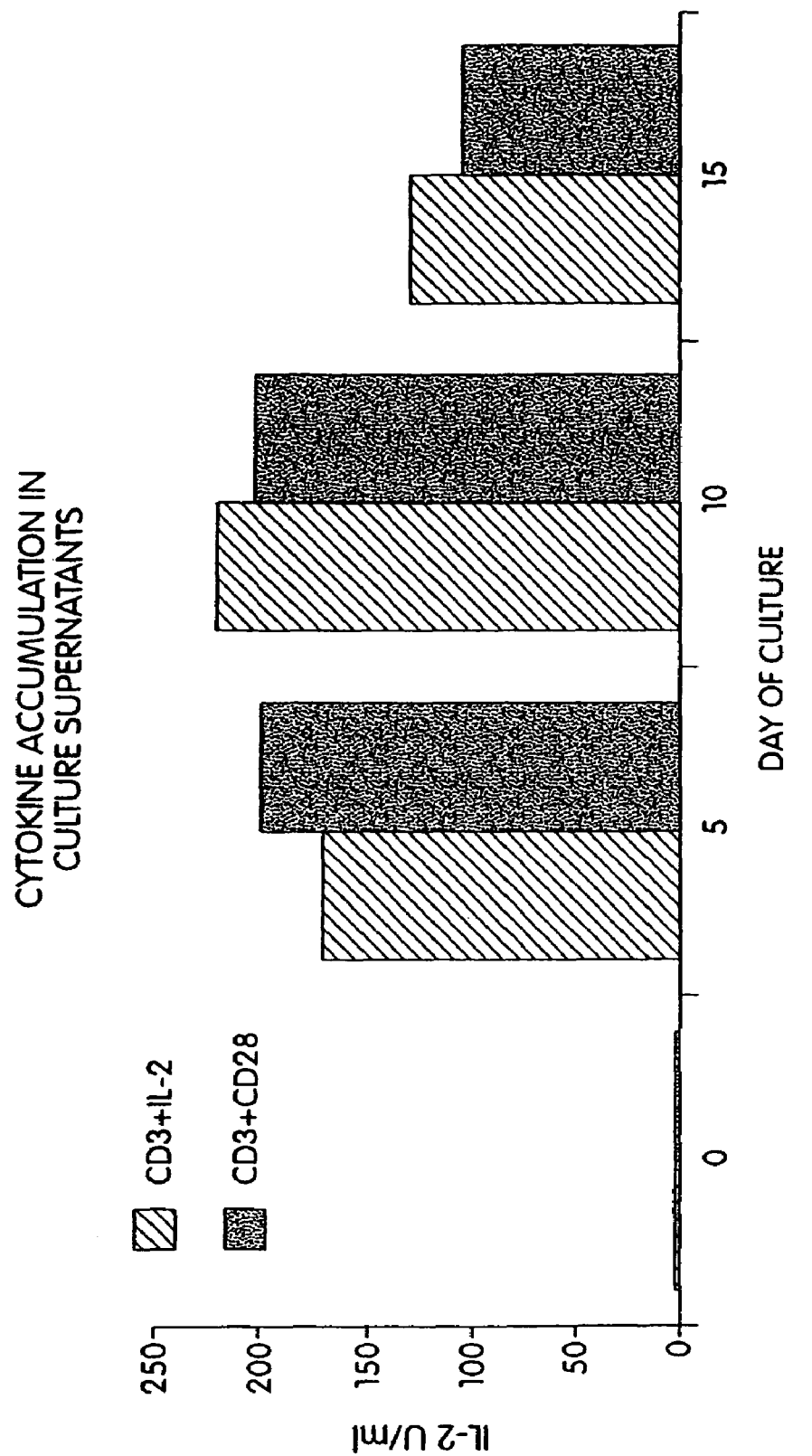
FIG. 11 is a bar graph depicting the amount of IL-2 produced by CD4+ T cells following stimulation with an anti-CD3 monoclonal antibody and an anti-CD28 monoclonal antibody or IL-2 over days in culture.
Figure 12:
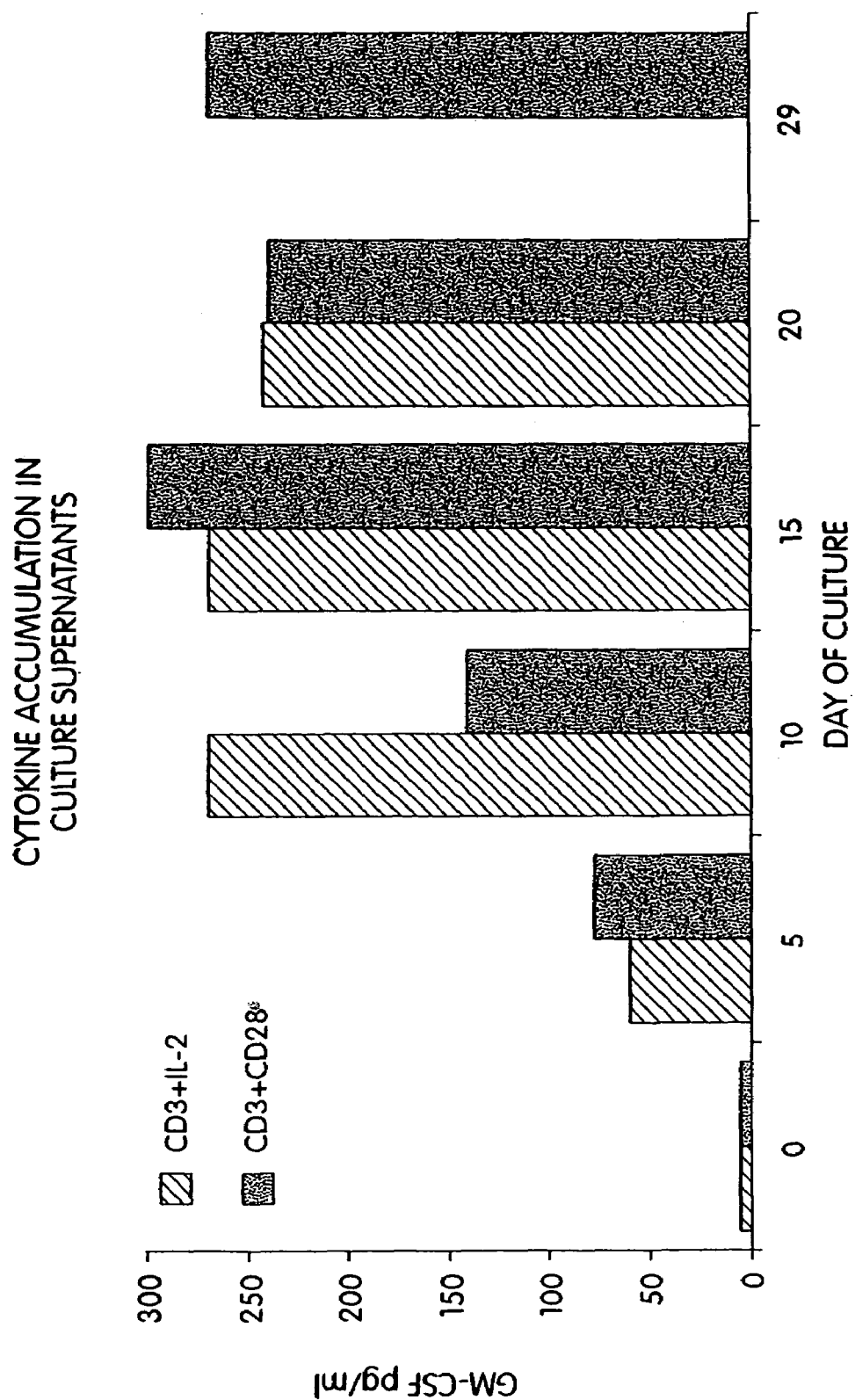
FIG. 12 is a bar graph depicting the amount of granulocyte-macrophage colony-stimulating factor (GM-CSF) produced by CD4+ T cells following stimulation with an anti-CD3 monoclonal antibody and an anti-CD28 monoclonal antibody or IL-2 over days in culture.
Figure 13:
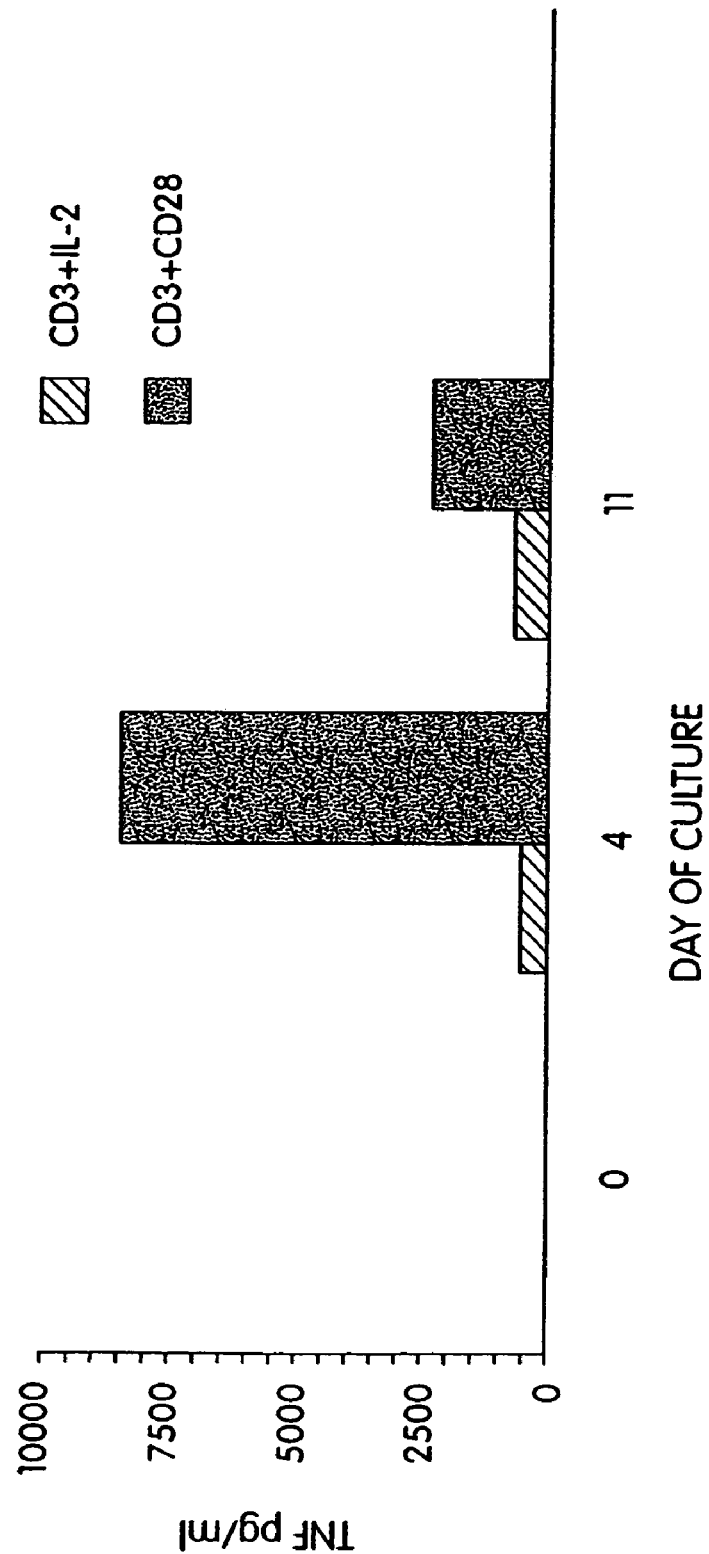
FIG. 13 is a bar graph depicting the amount of tumor necrosis factor (TNF) produced by CD4+ T cells following stimulation with an anti-CD3 monoclonal antibody and an anti-CD28 monoclonal antibody or IL-2 over days in culture.

Experiments were conducted to analyze the cytokines produced by T cells following anti-CD28 stimulation. $CD28^+/CD4^+$ T cells were isolated as described in the previous examples. The cells were stimulated with plastic immobilized anti-CD3 mAb and IL-2 (200 U/ml), or anti-CD3 and anti-CD28 without added lymphokine. The cells were restimulated with anti-CD3 antibody as determined by changes in cell volume as described in Example 5. Cell culture supernatant was removed at the time points indicated and analyzed for IL-2 (FIG. 11), GM-CSF (FIG. 12), and TNF-α (FIG. 13). IL-2 was determined by bioassay on CTLL-2 cells while TNF-α and GM-CSF were measured by ELISA according to manufacturers instructions (TNFα, GMCSF: R&D Systems, Minneapolis, Minn.). The data shown for the various cytokines are from separate experiments. In other experiments (not shown) anti-CD3 plus anti-CD28 stimulation was shown to cause high levels of IL-4 and IL-5 in culture supernatants after approximately day 10 of culture, although only small amounts of these cytokines were present during the early period of culture.

The patterns of cytokine secretion with cells expanded by several restimulations according to the protocol described in the examples was compared to cells expanded with anti-CD3 plus IL-2 over three weeks in culture. Cells were changed to fresh medium at each restimulation with anti-CD3 antibody. Stimulations were spaced at ten day intervals. After 24 hours of further culture, an aliquot of cell culture supernatant was removed for assay. ELISA assays for individual cytokines were performed with kits from various suppliers (IL-2: T Cell Diagnostics, Cambridge, Mass.; IFN-γ Endogen, Inc., Boston, Mass.; IL-4, TNFα, GMCSF: R&D Systems, Minneapolis, Minn.) according to directions supplied with the kits. As can be seen from the results of a representative experiment shown in Table 2, the two protocols result in very similar levels of IL-2 and IL-4 secretion. The higher levels of GM-CSF and TNFα secretion with anti-CD3 and anti-CD28 costimulation suggests that the proliferative capacity of this combination of stimuli may be due in part to its ability to stimulate an autocrine loop.

TABLE 2

Comparison of cytokines secreted by T cells expanded with anti-CD3 and IL-2 versus T cells expanded with anti-CD3 and anti-CD28.

| Stimulation cycle | Costimulus | Concentration of lymphokine in pg/ml | | | | |
|---|---|---|---|---|---|---|
| | | IL-2 | IFN-γ | IL-4 | GM-CSF | TNFα |
| S1 | IL-2 | 20714 | 1458 | 16 | 2303 | 789 |
| | αCD28 | 13794 | 2211 | 14 | 3812 | 3387 |
| S2 | IL-2 | 20250 | 16600 | 964 | 51251 | 3221 |
| | αCD28 | 28411 | 56600 | 1030 | 138207 | 13448 |
| S3 | IL-2 | 21282 | 8617 | 1153 | 86418 | 2899 |
| | αCD28 | 14129 | 12583 | 1044 | 120418 | 5969 |

EXAMPLE 7

Polyclonality of T Cells Following Anti-CD28 Stimulation

Figure 14:
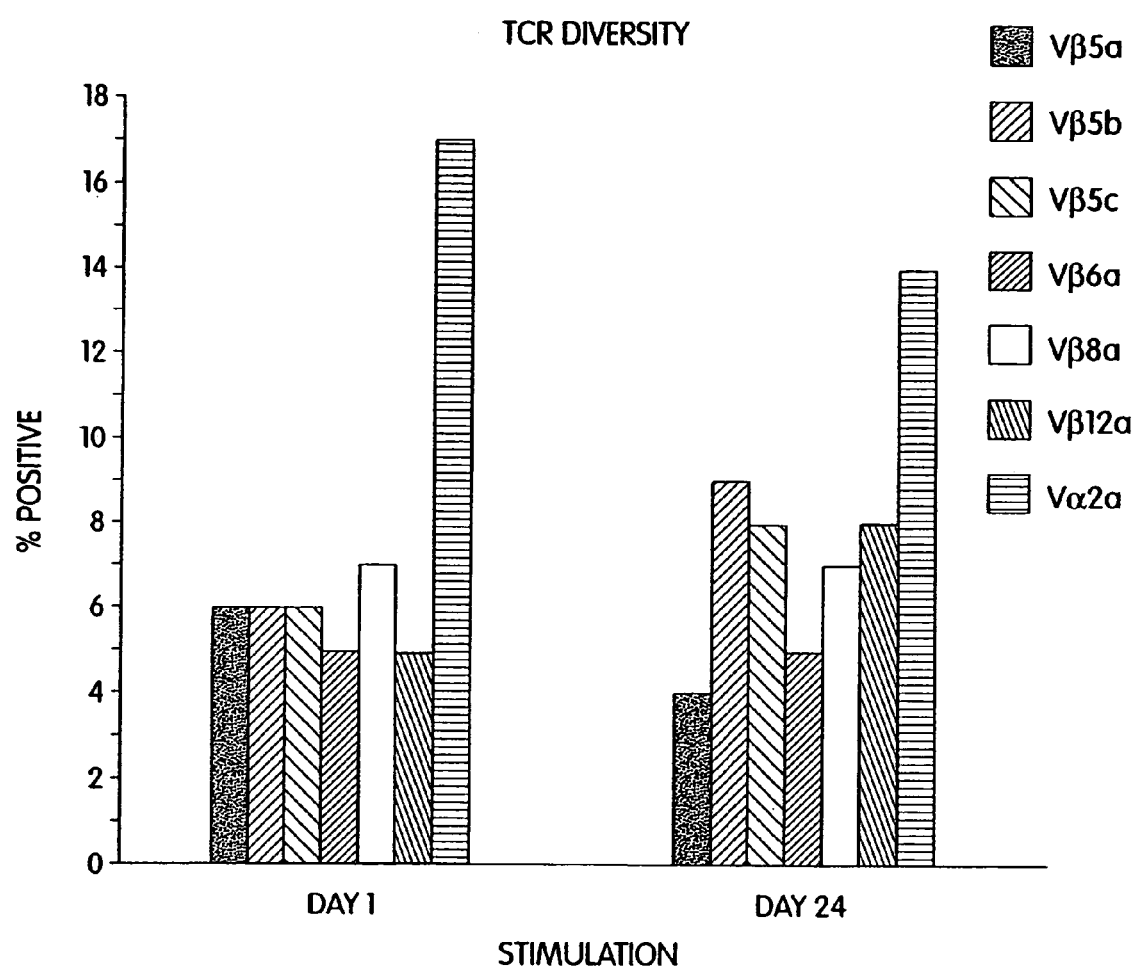
FIG. 14 is a bar graph depicting the T cell receptor (TCR) diversity in CD4+ T cells following stimulation with an anti-CD3 monoclonal antibody and an anti-CD28 monoclonal antibody at day 1 and day 24 of culture.

The polyclonality of a population of T cells following stimulation with an anti-CD3 and an anti-CD28 antibody as described in the preceding examples was determined. CD28+/CD4+ T cells were isolated as described in the previous examples. The cells were stimulated with plastic immobilized anti-CD3 mAb and anti-CD28 mAb and FACS analysis conducted essentially as described in Example 4 using a panel of anti-TCR antibodies (Vβ5a, Vβ5b, Vβ5c, Vβ6a, Vβ8a, Vβ12a and Vα2a) obtained from Pharmingen. The polyclonality of the T cell population was determined before (Day 1) and after stimulation (Day 24). As shown in FIG. 14, the TCR diversity of a population of T cells stimulated through CD28 is maintained at day 24.

EXAMPLE 8

Figure 15:
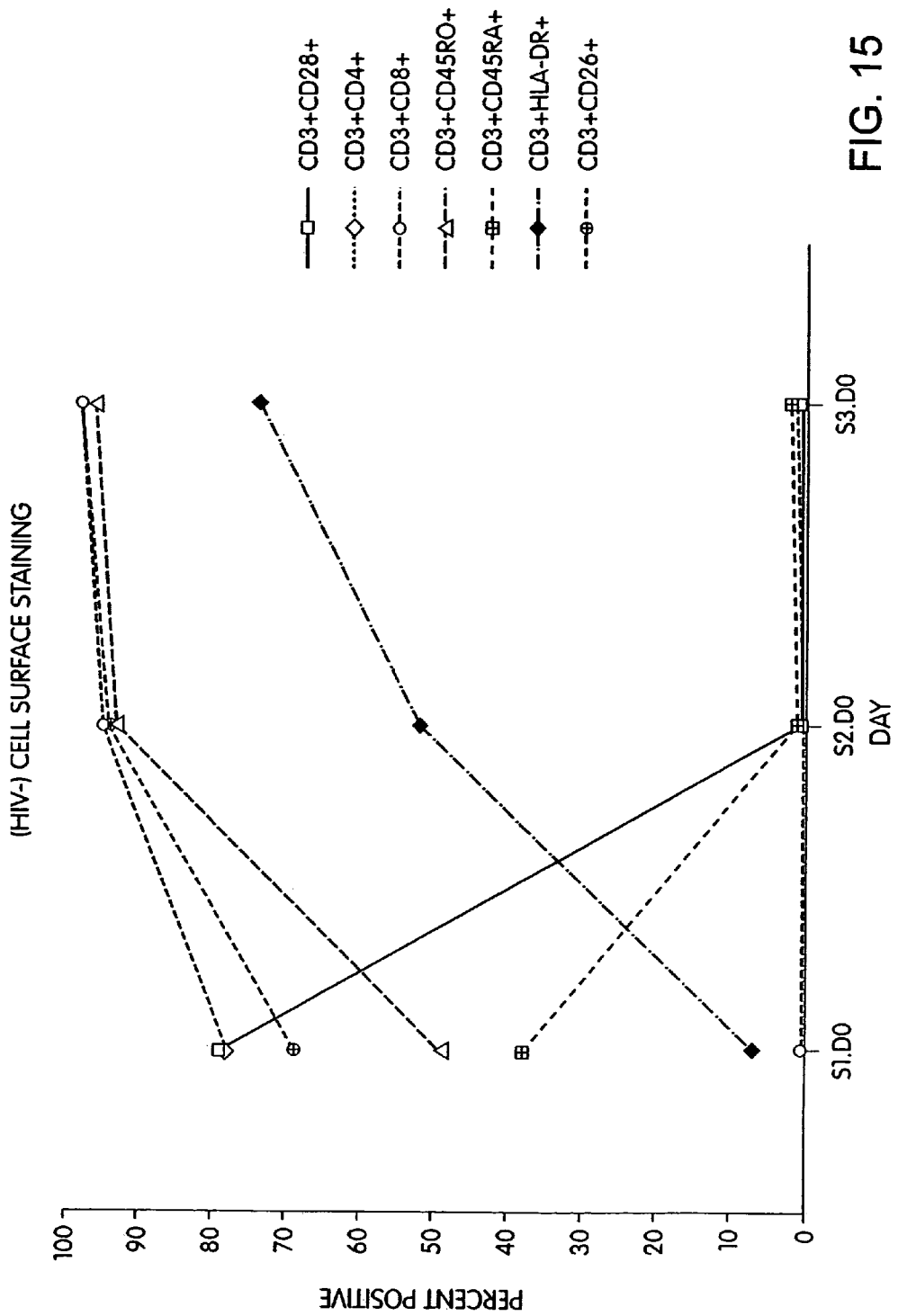
FIG. 15 depicts cell surface staining of CD4+ T cells obtained from an HIV seronegative individual following stimulation (S1, S2 and S2) with an anti-CD3 monoclonal antibody and an anti-CD28 monoclonal antibody over days in culture.
Figure 16:
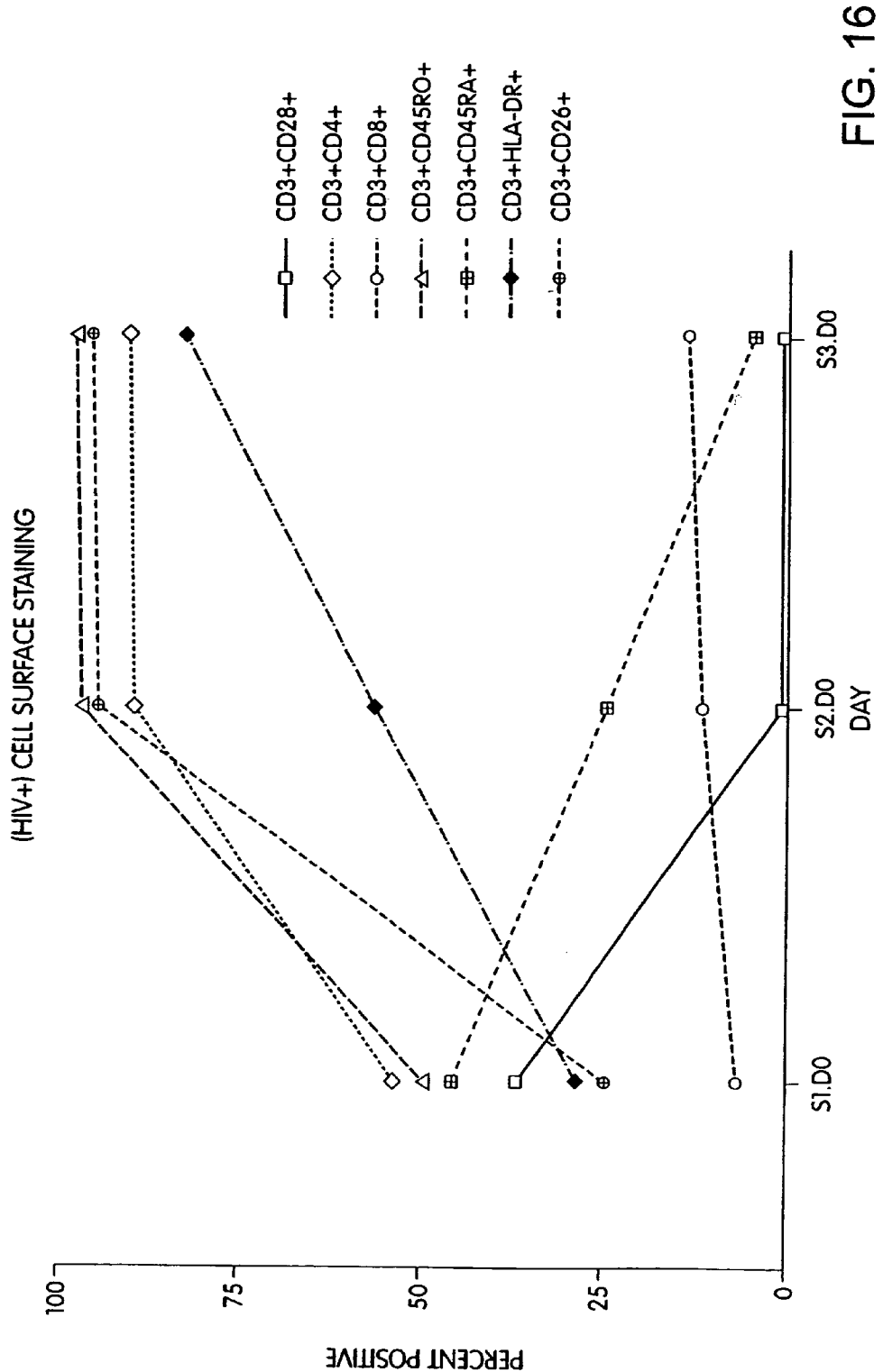
FIG. 16 depicts cell surface staining of CD4+ T cells obtained from an HIV seropositive individual following stimulation (S1, S2 and S2) with an anti-CD3 monoclonal antibody and an anti-CD28 monoclonal antibody over days in culture.

Comparison of Cell Surface Staining of T Cells from HIV+ and HIV− Individuals Following Anti-CD28 Stimulation Another series of experiments was conducted to determine the expression of various T cell surface markers on cells from HIV seropositive and seronegative individuals expanded according to the procedures described in the previous examples. CD28+/CD4+ T cells were obtained as described herein. In these experiments, the anti-CD3 mAb was labeled with a first label (e.g., rhodamine) and the appropriate second antibody (e.g., anti-CD28, anti-CD4, anti-CD8) was labeled with a second label (e.g., fluorescein). T cells were stimulated with plastic immobilized anti-CD3 mAb and anti-CD28 mAb as described herein and the percent of T cells expressing a variety of cell surface markers at differenct stimulations (i.e., S1, S2 and S2) determined by FACS analysis. As shown in FIGS. 15 and 16, the overall cell surface marker distribution on T cells obtained from HIV seropositive and seronegative individuals is approximately the same throughout the stimulation assay. It is noteworthy that the presence of one cell surface marker, CD45RA, which is a marker for naive T cells, declines over the course of CD28 stimulated T cell expansion. In contrast, the percent of T cells expressing the memory T cell surface marker, CD45RO, increases with CD28 stimulation. Thus, T cell expansion through CD28 stimulation preferentially expands memory T cells or converts naive T cells to memory T cells. It should be noted that the decline in the percent of T cells expressing CD28 is an artifact of the experiment due to the presence of anti-CD28 antibody in the T cell culture throughout the assay. The presence of anti-CD28 antibody prevents staining of the CD28 antigen.

EXAMPLE 9

Long Term Growth of CD8+ T cells With Anti-CD3 and Monoclonal Antibody 2D8

Figure 17:
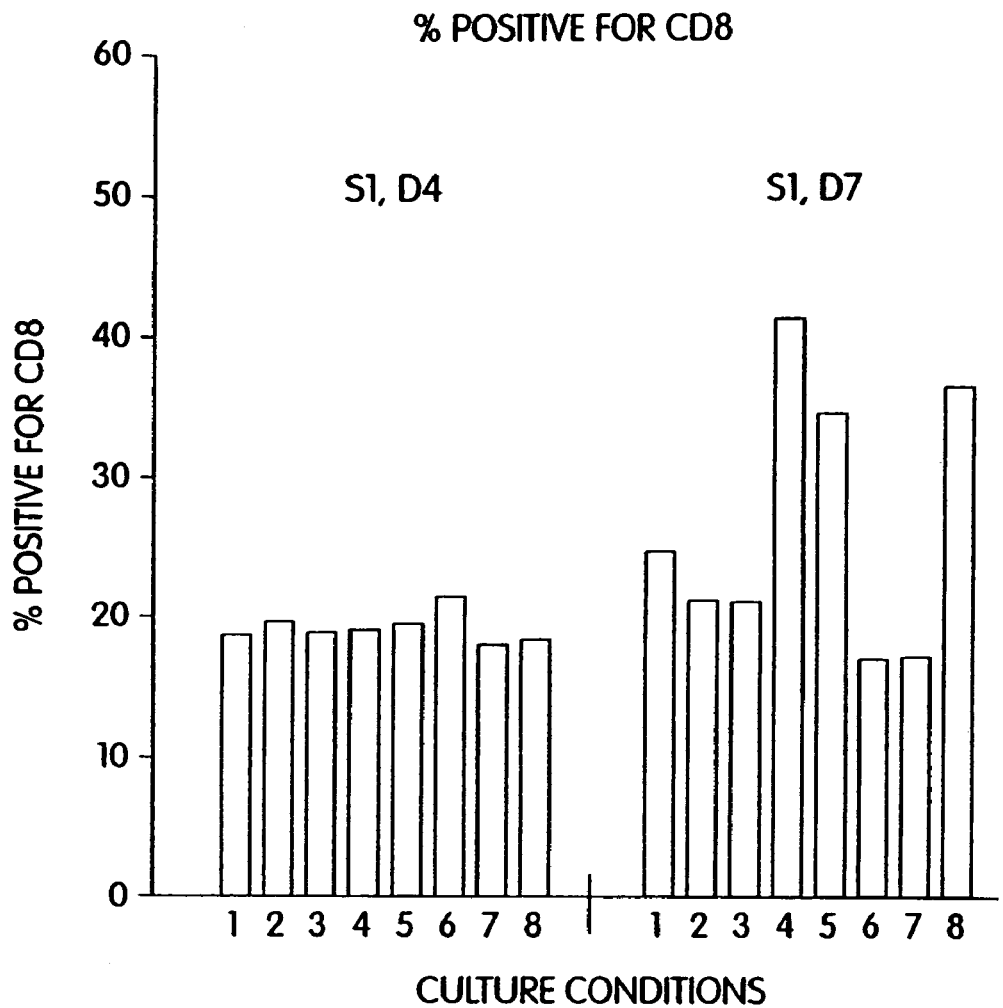
FIG. 17 depicts expansion of CD8+ T cells following stimulation with an anti-CD3 monoclonal antibody and an monoclonal antibody ES5.2D8 at day 4 and day 7 of culture.
Figure 18A:
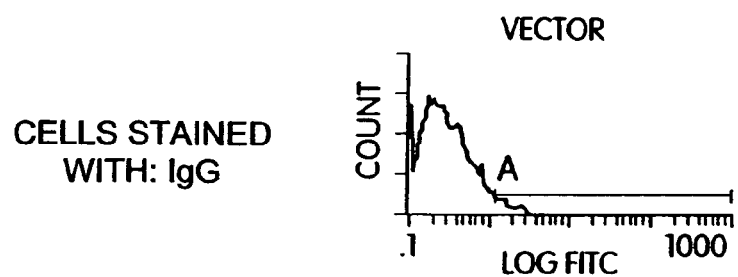
FIG. 18 shows FACS analysis of the monoclonal antibody ES5.2D8 (panels C and D) or a control IgG (panels A and B) depicting the binding reactivity with MOP cells transfected with a plasmid encoding the CD9 antigen.
Figure 18B:
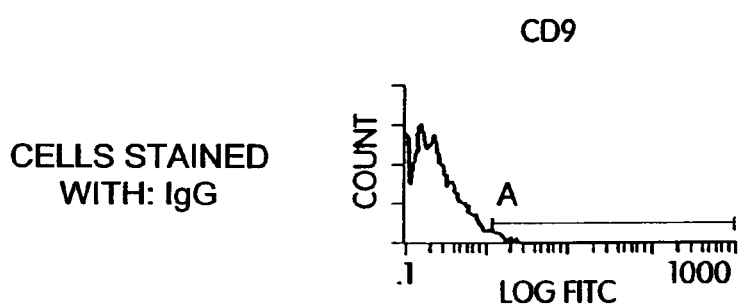
Figure 18C:
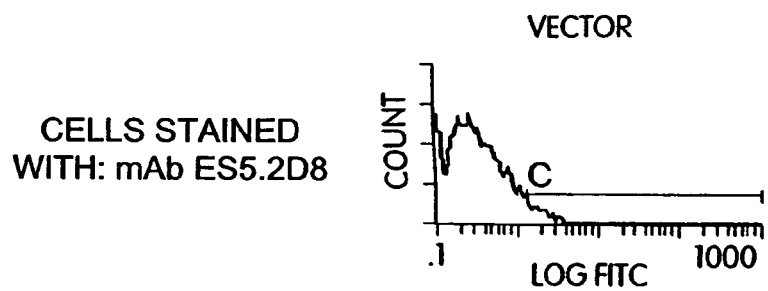
Figure 18D:
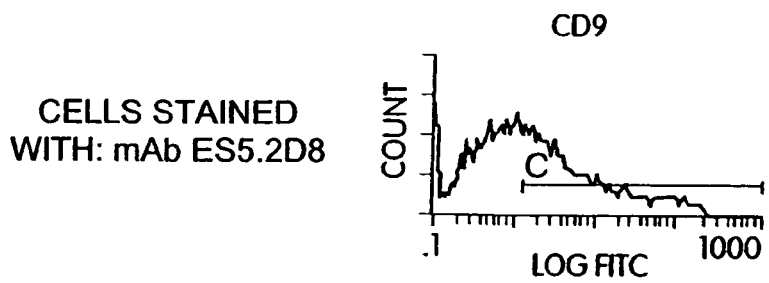

Experiments were conducted to determine whether a population of CD8+ T cells could be preferentially expanded by stimulation with an anti-CD3 mAb and a monoclonal antibody 2D8. CD28+ T cells were obtained essentially as described in Example 1. To assay for CD8 expression, a primary anti-CD8 antibody and a labeled appropriate secondary antibody were used in FACS analysis to determine the percent positive cells. As shown in FIG. 17, at day 7 following stimulation of T cells with the anti-CD3 mAb G19-4sp and the mAb 2d8, the CD8+ fraction had increased from approximately 20% to over 40%. Another monoclonal antibody ER4.7G11 (referred to as 7G11) was also found to stimulate CD8+ T cells. This antibody was raised against recombinant human CTLA4 and has been deposited with the ATCC on Jun. 3, 1994 at Accession No. HB 11642. This result indicates that binding of either a distinct region of CTLA4 or of a cross-reactive cell surface protein selectively activates CD8+ T cells.

EXAMPLE 10

Defining the Epitope of the Monoclonal Antibody 2D8 and Cloning the CD9 Antigen

To determine the epitope of the monoclonal antibody 2D8, epitope mapping was performed by phage display library (PDL) screening and was confirmed using synthetic peptides. A random 20 amino acid PDL was prepared by cloning a degenerate oligonucleotide into the fUSE5 vector (Scott, J. K. and Smith, G. P. (1990) *Science* 249:386–390) as described in Cwirla, S. E. et al. (1990) *Proc. Natl. Acad. Sci. USA* 87:6378–6382. The PDL was used to identify short peptides that specifically bound mAb 2D8 by a micropanning technique described in Jellis, C. L. et al. (1993) *Gene* 137:63–68. Individual phage clones were purified from the library by virtue of their affinity for immobilized mAb and the random peptide was identified by DNA sequencing.

Briefly, mAb 2D8 was coated onto Nunc Maxisorp 96 well plates and incubated with 5×10$^{10}$ phage representing 8×10$^{6}$ different phage displaying random 20 amino acid peptides. Specifically bound phage were eluted, amplified, then incubated with the antibody a second time. After the third round, 7 phage were isolated, and DNA was prepared for sequencing.

Sequence analysis of these clones demonstrated that three of the seven sequences were identical and a fourth was similar:

```
2D8#2    (SEQ ID NO: 1)    HQFCDHWGCWLLRETHLFTP

2D8#4    (SEQ ID NO: 2)    HQFCDHWGCWLLRETHIFTP

2D8#10   (SEQ ID NO: 3)    HQFCDHWGCWLLRETHIFTP

2D8#6    (SEQ ID NO: 4)    LRLVLEDPGIWLRPDYFFPA
```

Based on this data an epitope of G X W L X D/E (SEQ ID NO: 5) was proposed.

In addition to CTLA4, a second antigen for mAb 2D8 was discovered using cDNA expression cloning.

A. Construction of A cDNA Expression Library

A cDNA library was constructed in the pCDM8 vector (Seed, (1987) *Nature* 329:840) using poly (A)$^+$ RNA isolated from activated T cells as described (Aruffo et al. (1987) *Proc. Natl. Acad. Sci. USA* 84:3365). To prepare total RNA, T cells were harvested from culture and the cell pellet homogenized in a solution of 4 M guanidine thiocyanate, 0.5% sarkosyl, 25 mM EDTA, pH 7.5, 0.13% Sigma antifoam A, and 0.7% mercaptoethanol. RNA was purified from the homogenate by centrifugation for 24 hour at 32,000 rpm through a solution of 5.7 M CsCl, 10 mM EDTA, 25 mM Na acetate, pH 7. The pellet of RNA was dissolved in 5% sarkosyl, 1 mM EDTA, 10 mM Tris, pH 7.5 and extracted with two volumes of 50% phenol, 49% chloroform, 1% isoamyl alcohol. RNA was ethanol precipitated twice. Poly (A)$^+$ RNA used in cDNA library construction was purified by two cycles of oligo (dT)-cellulose selection.

Complementary DNA was synthesized from 5.5 µg of poly(A)$^+$ RNA in a reaction containing 50 mM Tris, pH 8.3, 75 mM KCl, 3 mM MgCl$_2$, 10 mM dithiothreitol, 500 µM dATP, dCTP, dGTP, dTTP, 50 µg/ml oligo(dT)$_{12-18}$, 180 units/ml RNasin, and 10,000 units/ml Moloney-MLV reverse transcriptase in a total volume of 55 µl at 37° C. for 1 hr. Following reverse transcription, the cDNA was converted to double-stranded DNA by adjusting the solution to 25 mM Tris, pH 8.3, 100 mM KCl, 5 mM MgCl$_2$, 250 µM each dATP, dCTP, dGTP, dTTP, 5 mM dithiothreitol, 250 units/ml DNA polymerase I, 8.5 units/ml ribonuclease H and incubating at 16° C. for 2 hr. EDTA was added to 18 mM and the solution was extracted with an equal volume of 50% phenol, 49% chloroform, 1% isoamyl alcohol. DNA was precipitated with two volumes of ethanol in the presence of 2.5 M ammonium acetate and with 4 micrograms of linear polyacrylamide as carrier. In addition, cDNA was synthesized from 4µg of poly(A)$^+$ RNA in a reaction containing 50 mM Tris, pH 8.8, 50 µg/ml oligo(dT)$_{12-18}$, 327 units/ml RNasin, and 952 units/ml AMV reverse transcriptase in a total volume of 100 µl at 42° C. for 0.67 hr. Following reverse transcription, the reverse transcriptase was inactivated by heating at 70° C. for 10 min. The cDNA was converted to double-stranded DNA by adding 320 µl H$_2$O and 80 µl of a solution of 0.1M Tris, pH 7.5, 25 mM MgCl$_2$, 0.5 M KCl, 250 µg/ml bovine serum albumin, and 50 mM dithiothreitol, and adjusting the solution to 200 µM each dATP, dCTP, dGTP, dTTP, 50 units/ml DNA polymerase I, 8 units/ml ribonuclease H and incubating at 16° C. for 2 hours. EDTA was added to 18 mM and the solution was extracted with an equal volume of 50% phenol, 49% chloroform, 1% isoamyl alcohol. DNA was precipitated with two volumes of ethanol in the presence of 2.5 M ammonium acetate and with 4 micrograms of linear polyacrylamide as carrier.

The DNA from 4 µg of AMV reverse transcription and 2.0 µg of Moloney MLV reverse transcription were combined. Non-selfcomplementary BstXI adaptors were added to the DNA as follows: The double-stranded cDNA from 6 µg of poly(A)$^+$ RNA was incubated with 3.6 µg of a kinased oligonucleotide of the sequence CTTTAGAGCACA (SEQ ID NO: 10) and 2.4 µg of a kinased oligonucleotide of the sequence CTCTAAAG in a solution containing 6 mM Tris, pH 7.5, 6 mM MgCl$_2$, 5 mM NaCl, 350 µg/ml bovine serum albumin, 7 mM mercaptoethanol, 0.1 mM ATP, 2 mM dithiothreitol, 1 mM spermidine, and 600 units T4 DNA ligase in a total volume of 0.45 ml at 15° C. for 16 hours. EDTA was added to 34 mM and the solution was extracted with an equal volume of 50% phenol, 49% chloroform, 1% isoamyl alcohol. DNA was precipitated with two volumes of ethanol in the presence of 2.5 M ammonium acetate.

DNA larger than 600 bp was selected as follows: The adaptored DNA was redissolved in 10 mM Tris, pH 8, 1 mM EDTA, 600 mM NaCl, 0.1% sarkosyl and chromatographed on a Sepharose CL-4B column in the same buffer. DNA in the void volume of the column (containing DNA greater than 600 bp) was pooled and ethanol precipitated.

The pCDM8 vector was prepared for cDNA cloning by digestion with BstXI and purification on an agarose gel. Adaptored cDNA from 6 µg of poly(A)$^+$ RNA was ligated to 2.25 µg of BstXI cut pCDM8 in a solution containing 6 mM Tris, pH 7.5, 6 mM MgCl$_2$, 5 mM NaCl, 350 µg/ml bovine serum albumin, 7 mM mercaptoethanol, 0.1 mM ATP, 2 mM dithiothreitol, 1 mM spermidine, and 600 units T4 DNA ligase in a total volume of 1.5 ml at 15° C. for 24 hr. The ligation reaction mixture was then transformed into competent *E. coli* DH10B/P3 by standard techniques.

Plasmid DNA was prepared from a 500 ml culture of the original transformation of the cDNA library. Plasmid DNA was purified by the alkaline lysis procedure followed by twice banding in CsCl equilibrium gradients (Maniatis et al, *Molecular Cloning: A Laboratory Manual,* Cold Spring Harbor, N.Y. (1987)).

B. Cloning Procedure

In the cloning procedure, the cDNA expression library was introduced into MOP8 cells (ATCC No. CRL1709) using lipofectamine and the cells screened with mAb 2D8 to identify transfectants expressing a 2D8 ligand on their surface. In the first round of screening, thirty 100 mm dishes of 50% confluent COS cells were transfected with 0.05 µg/ml activated T cell library DNA using the DEAE-Dextran method (Seed, B. et al. (1987) *Proc. Natl. Acad. Sci. USA* 84:3365). The cells were trypsinized and re-plated after 24 hours. After 47 hours, the cells were detached by incubation in PBS/0.5 mM EDTA, pH 7.4/0.02% Na azide at 37° C. for 30 min.

Detached cells were treated with 10 µg/ml mAb 2D8. Cells were incubated with the monoclonal antibody for 45 minutes at 4° C. Cells were washed and distributed into panning dishes coated with affinity-purified goat anti-mouse IgG antibody and allowed to attach at room temperature.

After 3 hours, the plates were gently washed twice with PBS/0.5 mM EDTA, pH 7.4/0.02% Na azide, 5% FCS and once with 0.15 M NaCl, 0.01 M Hepes, pH 7.4, 5% FCS. Unbound cells were thus removed and episomal DNA was recovered from the adherent panned cells by conventional techniques.

Episomal DNA was transformed into *E. coli* DH10B/P3. The plasmid DNA was re-introduced into MOP8 cells using lipofectamine and the cycle of expression and panning was repeated twice. Cells expressing a 2D8 ligand were selected by panning on dishes coated with goat anti-mouse IgG antibody. After the third round of screening, plasmid DNA was prepared from individual colonies and transfected into MOP8 cells by the DEAE-Dextran method. Expression of a 2D8 ligand on transfected MOP8 cells was analyzed by indirect immunofluorescence with mAb 2D8 (See FIG. 18).

DNA from one clone (mp5) identified as positive by FACS analysis was sequenced using standard techniques. FASTA analysis of the amino acid sequence of mp5 identified a matching protein, CD9, in the GCG data banks. The full amino acid sequence of CD9 is shown below (SEQ ID NO: 6).

BESTFIT analysis of the phage epitopes of mAb 2D8 to the amino acid sequence of CD9 revealed a close match:

```
    GCWLLRE    (phage 2D8#2, 4, 10; SEQ ID NO: 7)
    GIWLRPD    (phage 2D8#6; SEQ ID NO: 8)
    GLWLRFD    (CD9 sequence; SEQ ID NO: 9)
FT  DOMAIN    111  194   EXTRACELLULAR (PROBABLE)
FT  TRANSMEM  195  220   POTENTIAL
FT  DOMAIN    221  227   CYTOPLASMIC (PROBABLE)
```

```
-continued
FT  CARBOHYD   51   51   POTENTIAL
FT  CARBOHYD   52   52   POTENTIAL
FT  CONFLICT    8    8   C → S (IN REF. 1)
FT  CONFLICT   66   66   G → A (IN REF. 1)
FT  CONFLICT  193  193   MISSING (IN REF. 1)
SQ  SEQUENCE  227 AA; 25285 MW; 261251 CN;

Cd9_Human Length: 227 May 25, 1994 14:10 Type: P
Check: 1577

(SEQ ID NO: 6)
  1  PVKGGTKCIK YLLFGFNFIF WLAGIAVLAI GLWLRFDSQT
     KSIFEQETNN

51  NNSSFYTGVY ILIGAGALMM LVGFLGCCGA VQESQCMLGL
     FFGFLLVIFA

101  IEIAAAIWGY SHKDEVIKEV QEFYKDTYNK LKTKDEPQRE
     TLKAIHYALN

151  CCGLAGGVEQ FISDICPKKD VLETFTVKSC PDAIKEVFDN
     KFHIIGAVGI

201  GIAVVMIFGM IFSMILCCAI RRNREMV
```

EQUIVALENTS

Those skilled in the art will recognize, or be able to ascertain using no more than routine experimentation, many equivalents to the specific embodiments of the invention described herein. Such equivalents are intended to be encompassed by the following claims.

---

(ii) MOLECULE TYPE: peptide (xi) SEQUENCE DESCRIPTION: SEQ ID NO: 4:

```
Leu Arg Leu Val Leu Glu Asp Pro Gly Ile Trp Leu Arg Pro Asp Tyr
              5                  10                  15
Phe Phe Pro Ala
         20
```

(2) INFORMATION FOR SEQ ID NO: 5:

(i) SEQUENCE CHARACTERISTICS:

```
atg acg gcc ggg cag ctt ctg cgc acc gag cca tca gcc cag ccc cag     48
Met Thr Ala Gly Gln Leu Leu Arg Thr Glu Pro Ser Ala Gln Pro Gln
 1               5                  10                  15 cgg gtg cgc cac agc acc ccg ccg gcg gca ctc caa gca gac atc gtg     96
Arg Val Arg His Ser Thr Pro Pro Ala Ala Leu Gln Ala Asp Ile Val
                20                  25                  30 ccg tcg tac ccg ccg ccc gag tcg gac ggt gac gag tcg tgg gtc tgg    144
Pro Ser Tyr Pro Pro Pro Glu Ser Asp Gly Asp Glu Ser Trp Val Trp
            35                  40                  45 tcc cag atc aag gcg gag gcg cgg cgc gac gcg gac gcg gag ccg gcg    192
Ser Gln Ile Lys Ala Glu Ala Arg Arg Asp Ala Asp Ala Glu Pro Ala
        50                  55                  60 ctg gcc tcc ttc ctc tac gcg acg gtg ctg tcg cac gcg tcc ctg gac    240
Leu Ala Ser Phe Leu Tyr Ala Thr Val Leu Ser His Ala Ser Leu Asp
```

-continued

| | |
|---|---|
| cgg tcc ctg gcc ttc cac ctg gcc aac aag ctg tgc tcc tcc acg ctg<br>Arg Ser Leu Ala Phe His Leu Ala Asn Lys Leu Cys Ser Ser Thr Leu<br>                              85                          90                    95 | 288 |
| ctg tcg acg ctc tct aac gac ctc ttc gtg gcg tcg ctc gcg gag cac<br>Leu Ser Thr Leu Ser Asn Asp Leu Phe Val Ala Ser Leu Ala Glu His<br>                      100                      105                  110 | 336 |
| ccg tcg tcc gcg cgg cgg cgg tgg cga cct gat cgc cgc gcg gtc gcg<br>Pro Ser Ser Ala Arg Arg Arg Trp Arg Pro Asp Arg Arg Ala Val Ala<br>               115                    120                    125 | 384 |
| gga ccc ggc tgc gcg ggc ttc gcg cac tgc ctc ctc aac tac aag ggg<br>Gly Pro Gly Cys Ala Gly Phe Ala His Cys Leu Leu Asn Tyr Lys Gly<br>130                      135                    140 | 432 |
| ttc ctg gcc gtg cag gcg cac cgc gtg gcg cac gtg ctg tgg gcg cag<br>Phe Leu Ala Val Gln Ala His Arg Val Ala His Val Leu Trp Ala Gln<br>145                      150                    155                  160 | 480 |
| ggc cgg cgc gcg ctg gcg ctg gcg ctc cag tcc cgc gtc gcc gag gtc<br>Gly Arg Arg Ala Leu Ala Leu Ala Leu Gln Ser Arg Val Ala Glu Val<br>               165                    170                    175 | 528 |
| ttc gcc gtg gac atc cac ccg gcc gcc acc gtc ggc agg ggc atc ctg<br>Phe Ala Val Asp Ile His Pro Ala Ala Thr Val Gly Arg Gly Ile Leu<br>                    180                      185                  190 | 576 |
| ctc gac cac gcc acg ggc gtc gtc gtc ggg gag acg gcc gtc gtg ggc<br>Leu Asp His Ala Thr Gly Val Val Val Gly Glu Thr Ala Val Val Gly<br>               195                    200                    205 | 624 |
| gac aac gtc tcc ata ctc cac cac gtg acg ttg gcg gca ccg gca agg<br>Asp Asn Val Ser Ile Leu His His Val Thr Leu Ala Ala Pro Ala Arg<br>210                      215                    220 | 672 |
| cgt tgg cga ccg gca ccc caa gat cgg gac ggc gtg ctc atc ggc gcc<br>Arg Trp Arg Pro Ala Pro Gln Asp Arg Asp Gly Val Leu Ile Gly Ala<br>225                      230                    235                  240 | 720 |
| ggc gcg acc gtc ctc gga aac gtc agg atc ggc gcc ggc gcc aag gtc<br>Gly Ala Thr Val Leu Gly Asn Val Arg Ile Gly Ala Gly Ala Lys Val<br>                    245                      250                  255 | 768 |
| ggc gcc ggg tcc gtc gtg ctc atc gac gtg ccg ccc agg agc acc gcc<br>Gly Ala Gly Ser Val Val Leu Ile Asp Val Pro Pro Arg Ser Thr Ala<br>                    260                      265                  270 | 816 |
| gtg ggg aac ccc gcc agg ctg atc ggc ggg aag aag ggc gag gag gtg<br>Val Gly Asn Pro Ala Arg Leu Ile Gly Gly Lys Lys Gly Glu Glu Val<br>275                      280                    285 | 864 |
| atg ccg ggg gag tcc atg gac cac acc tcc ttc ata cag cag tgg tcg<br>Met Pro Gly Glu Ser Met Asp His Thr Ser Phe Ile Gln Gln Trp Ser<br>290                      295                    300 | 912 |
| gac tac atc att t ga<br>Asp Tyr Ile Ile<br>305 | 927 |

<210> SEQ ID NO 2
<211> LENGTH: 308
<212> TYPE: PRT
<213> ORGANISM: Zea mays

<400> SEQUENCE: 2

Met Thr Ala Gly Gln Leu Leu Arg Thr Glu Pro Ser Ala Gln Pro Gln
1                 5                        10                        15

Arg Val Arg His Ser Thr Pro Ala Ala Leu Gln Ala Asp Ile Val
                   20                      25                      30

Pro Ser Tyr Pro Pro Pro Glu Ser Asp Gly Asp Glu Ser Trp Val Trp
          35                      40                      45

-continued

| | | | | | | | | | | | | | | |
|---|---|---|---|---|---|---|---|---|---|---|---|---|---|---|
| Ser | Gln | Ile | Lys | Ala | Glu | Ala | Arg | Arg | Asp | Ala | Asp | Ala | Glu | Pro | Ala |
| | 50 | | | | 55 | | | | 60 | | | | | | |
| Leu | Ala | Ser | Phe | Leu | Tyr | Ala | Thr | Val | Leu | Ser | His | Ala | Ser | Leu | Asp |
| 65 | | | | 70 | | | | 75 | | | | | | 80 | |
| Arg | Ser | Leu | Ala | Phe | His | Leu | Ala | Asn | Lys | Leu | Cys | Ser | Ser | Thr | Leu |
| | | | 85 | | | | | 90 | | | | | 95 | | |
| Leu | Ser | Thr | Leu | Ser | Asn | Asp | Leu | Phe | Val | Ala | Ser | Leu | Ala | Glu | His |
| | | 100 | | | | | 105 | | | | | 110 | | | |
| Pro | Ser | Ser | Ala | Arg | Arg | Trp | Arg | Pro | Asp | Arg | Arg | Ala | Val | Ala |
| | 115 | | | | | 120 | | | | 125 | | | | |
| Gly | Pro | Gly | Cys | Ala | Gly | Phe | Ala | His | Cys | Leu | Leu | Asn | Tyr | Lys | Gly |
| | 130 | | | | 135 | | | | | 140 | | | | | |
| Phe | Leu | Ala | Val | Gln | Ala | His | Arg | Val | Ala | His | Val | Leu | Trp | Ala | Gln |
| 145 | | | | 150 | | | | | 155 | | | | | 160 | |
| Gly | Arg | Arg | Ala | Leu | Ala | Leu | Ala | Leu | Gln | Ser | Arg | Val | Ala | Glu | Val |
| | | | 165 | | | | 170 | | | | | 175 | | | |
| Phe | Ala | Val | Asp | Ile | His | Pro | Ala | Ala | Thr | Val | Gly | Arg | Gly | Ile | Leu |
| | | | 180 | | | | 185 | | | | | 190 | | | |
| Leu | Asp | His | Ala | Thr | Gly | Val | Val | Val | Gly | Glu | Thr | Ala | Val | Val | Gly |
| | | 195 | | | | 200 | | | | | 205 | | | | |
| Asp | Asn | Val | Ser | Ile | Leu | His | His | Val | Thr | Leu | Ala | Ala | Pro | Ala | Arg |
| | | | | | | | | 12 | | | | | | | |

The invention claimed is:

1. A method for inducing a population of T cells to proliferate to sufficient numbers for use in therapy, comprising:
   (a) activating a population of T cells in vitro with an agent which stimulates a TCR/CD3 complex-associated signal in the T cells, wherein the agent is selected from the group consisting of an anti-CD3 antibody or a CD3-binding fragment thereof, an anti-CD2 antibody or a CD2-binding fragment thereof, and an antigen in a form suitable to trigger a primary activation signal in the T cell when complexed with the TCR/CD3 complex, wherein said agent is attached on a surface; and
   (b) stimulating a CD28 accessory molecule on the surface of the T cells in vitro with a ligand that binds the CD28 accessory molecule on the surface of the T cells, wherein the ligand is selected from the group consisting of an anti-CD28 antibody or a CD28-binding fragment thereof, B7-1 or a CD28-binding fragment thereof, and B7-2 or a CD28-binding fragment thereof, wherein said ligand is attached on the same surface as said agent;
the activating and stimulating steps thereby inducing proliferation of the T cells to sufficient numbers for use in therapy.

2. The method of claim 1, wherein the agent which stimulates a TCR/CD3 complex-associated signal in the T cells is an anti-CD3 antibody or a CD3-binding fragment thereof.

3. The method of claim 2, wherein the anti-CD3 antibody or the CD3-binding fragment thereof is an anti-human CD3 monoclonal antibody or a CD3-binding fragment thereof.

4. The method of claim 3, wherein the anti-CD3 antibody is OKT3.

5. The method of claim 1, wherein the T cells are activated by contact with an antigen or portion thereof.

6. The method of claim 1, wherein the ligand is an anti-CD28 antibody or a CD28-binding fragment thereof.

7. The method of claim 6, wherein said anti-CD28 antibody is a whole antibody.

8. The method of claim 6, wherein the anti-CD28 antibody or the CD28-binding fragment thereof is an anti-human CD28 monoclonal antibody or a CD28-binding fragment thereof.

9. The method of claim 8, wherein the anti-CD28 antibody is EX5.3D10, produced by hybridoma cell line ATCC No. HB11373.

10. The method of claim 1, wherein the agent which stimulates a TCR/CD3 complex-associated signal in the T cells and the ligand that binds the CD28 accessory molecule on the surface of the T cells are attached on the same surface via a covalent modification.

11. The method of claim 1, wherein the agent which stimulates a TCR/CD3 complex-associated signal in the T cells and the ligand that binds the CD28 accessory molecule on the surface of the T cells are attached on the same surface via an avidin-biotin complex.

12. The method of claim 1, wherein the agent which stimulates a TCR/CD3 complex-associated signal in the T cells and the ligand that binds the CD28 accessory molecule on the surface of the T cells are attached on the same surface via a streptavidin-biotin complex.

13. The method of claim 1, wherein the agent which stimulates a TCR/CD3 complex-associated signal in the T cells and the ligand that binds the CD28 accessory molecule on the surface of the T cells are directly attached on the same surface.

14. The method of claim 1, wherein the surface is a bead.

15. The method of claim 14, wherein the bead is a magnetic immunobead.

16. The method of claim 1, wherein the surface is a tissue culture dish.

17. The method of claim 1, wherein the T cells are induced to proliferate for at least 3 days.

18. The method of claim 1, wherein the T cells are induced to proliferate for at least 7 days.

19. The method of claim 1, wherein the T cells are induced to proliferate to about 10-fold the original T cell population.

20. The method of claim 1, wherein the T cells are induced to proliferate to about 100-fold the original T cell population.

21. The method of claim 1, wherein the T cells are induced to proliferate to about 1000-fold the original T cell population.

22. The method of claim 1, wherein the population of T cells is increased in number from about 10- to about 1000-fold the original T cell population.

23. The method of claim 1, wherein the T cells are induced to proliferate to about 100,000-fold the original T cell population.

24. The method of claim 1, further comprising reactivating and re-stimulating the T cells with the agent and the ligand when the rate of T cell proliferation has decreased to induce further proliferation of the T cells to produce a population of T cells increased in number of from about 100- to about 100,000-fold the original T cell population.

25. The method of claim 24, wherein the rate of T cell proliferation is monitored by examining cell size.

26. The method of claim 1, wherein the population of T cells comprises $CD4^+$ T cells.

27. The method of claim 1, wherein the population of T cells is obtained from an individual infected with HIV.

28. The method of claim 27, wherein the method further comprises rendering the T cells resistant to HIV infection and restoring the T cells to the individual.

29. The method of claim 28, wherein the T cells are rendered resistant to HIV infection by contacting the T cells with at least one anti-retroviral agent which inhibits HIV replication or viral production.

30. The method of claim 28, wherein the T cells are rendered resistant to HIV infection by genetically transducing the T cells to produce molecules which inhibit HIV infection or replication.

31. An ex vivo method for inducing a population of $CD4^+$ T cells to proliferate to sufficient numbers for use in therapy, comprising:
(a) activating a population of $CD4^+$ T cells with an agent which stimulates a TCR/CD3 complex-associated signal in the $CD4^+$ T cells, wherein the agent is selected from the group consisting of an anti-CD3 antibody or a CD3-binding fragment thereof, an anti-CD2 antibody or a CD2-binding fragment thereof, and an antigen in a form suitable to trigger a primary activation signal in the T cell when complexed with the TCR/CD3 complex, wherein the agent is attached on a surface; and
(b) stimulating a CD28 accessory molecule on the surface of the T cells with a ligand that binds the CD28 accessory molecule on the surface of the T cells, wherein the ligand is selected from the group consisting of an anti-CD28 antibody or a CD28-binding fragment thereof, B7-1 or a CD28-binding fragment thereof, and B7-2 or a CD28-binding fragment thereof, wherein the ligand is attached on the same surface as said agent, the activating and stimulating steps thereby inducing proliferation of the $CD4^+$ T cells to sufficient numbers for use in therapy, and resulting in a population of $CD4^+$ T cells that are polyclonal with respect to antigen reactivity.

32. The method of claim 31, wherein the agent which stimulates a TCR/CD3 complex-associated signal in the T cells is an anti-CD3 antibody or a CD3-binding fragment thereof.

33. The method of claim 32, wherein the anti-CD3 antibody or CD3-binding fragment thereof is an anti-human CD3 monoclonal antibody or a CD3-binding fragment thereof.

34. The method of claim 33, wherein the anti-CD3 antibody is OKT3.

35. The method of claim 31, wherein the T cells are activated by contact with an antigen or portion thereof.

36. The method of claim 31, wherein the ligand is an anti-CD28 antibody or a CD28-binding fragment thereof.

37. The method of claim 31, wherein the anti-CD28 antibody is an anti-human CD28 monoclonal antibody or a CD28-binding fragment thereof.

38. The method of claim 37, wherein the anti-CD28 antibody is EX5.3D10, produced by hybridoma cell line ATCC No. HB11373.

39. The method of claim 31, wherein the agent which stimulates a TCR/CD3 complex-associated signal in the T cells and the ligand that binds the CD28 accessory molecule on the surface of the $CD4^+$ T cells are attached on the same surface via a covalent modification.

40. The method of claim 31, wherein the agent which stimulates a TCR/CD3 complex-associated signal in the $CD4^+$ T cells and the ligand that binds the CD28 accessory molecule on the surface of the $CD4^+$ T cells are attached on the same surface via an avidin-biotin complex.

41. The method of claim 31, wherein the agent which stimulates a TCR/CD3 complex-associated signal in the $CD4^+$ T cells and the ligand that binds the CD28 accessory molecule on the surface of the $CD4^+$ T cells are attached on the same surface via a streptavidin-biotin complex.

42. The method of claim 31, wherein the agent which stimulates a TCR/CD3 complex-associated signal in the $CD4^+$ T cells and the ligand that binds the CD28 accessory molecule on the surface of the $CD4^+$ T cells are directly attached on the same surface.

43. The method of claim 31, wherein the surface is a bead.

44. The method of claim 43, wherein the bead is a magnetic immunobead.

45. The method of claim 31, wherein the surface is a tissue culture dish.

46. The method of claim 31, wherein the $CD4^+$ T cells are induced to proliferate for at least 3 days.

47. The method of claim 31, wherein the $CD4^+$ T cells are induced to proliferate for at least 7 days.

48. The method of claim 31, wherein the $CD4^+$ T cells are induced to proliferate to about 10-fold the original $CD4^+$ T cell population.

49. The method of claim 31, wherein the $CD4^+$ T cells are induced to proliferate to about 100-fold the original $CD4^+$ T cell population.

50. The method of claim 31, wherein the $CD4^+$ T cells are induced to proliferate to about 1000-fold the original $CD4^+$ T cell population.

51. The method of claim 31, wherein the population of $CD4^+$ T cells is increased in number from about 10- to about 1000-fold the original $CD4^+$ T cell population.

52. The method of claim 31, wherein the $CD4^+$ T cells are induced to proliferate to about 100,000-fold the original $CD4^+$ T cell population.

53. The method of claim 31, further comprising reactivating and re-stimulating the $CD4^+$ T cells with the agent and the ligand when the rate of $CD4^+$ T cell proliferation has decreased to induce further proliferation of the CD4+ T cells to produce a population of CD4+ T cells increased in number of from about 100- to about 100,000-fold the original CD4+ T cell population.

54. The method of claim 31, wherein the population of CD4+ T cells is obtained from an individual infected with HIV.

55. The method of claim 31, wherein the method further comprises rendering the CD4+ T cells resistant to HIV infection and restoring the CD4+ T cells to the individual.

56. The method of claim 55, wherein the CD4+ T cells are rendered resistant to HIV infection by contacting the CD4+ T cells with at least one anti-retroviral agent which inhibits HIV replication or viral production.

57. The method of claim 55, wherein the CD4+ T cells are rendered resistant to HIV infection by genetically transducing the CD4+ T cells to produce molecules which inhibit HIV infection or replication.

58. The method of claim 1, wherein T cell proliferation is monitored by examining cell size.

59. The method of claim 31, wherein T cell proliferation is monitored by examining cell size.

60. The method of claim 1, wherein T cell proliferation is monitored by determining the level of expression of a cell surface molecule.

61. The method of claim 31, wherein T cell proliferation is monitored by determining the level of expression of a cell surface molecule.

62. A method for expanding a population of T cells to sufficient numbers for use in therapy, comprising:
   a) activating the population of T cells by contacting the T cells in vitro with an anti-CD3 antibody or a CD3-binding fragment thereof, which is attached on a surface; and
   b) stimulating a CD28 accessory molecule on the surface of the T cells in vitro with an anti-CD28 antibody or a CD28-binding fragment thereof, wherein said anti-CD28 antibody or CD28-binding fragment thereof is attached on the same surface as the anti-CD3 antibody or CD3-binding fragment thereof, the activating and stimulating steps thereby expanding the population of the T cells to sufficient numbers for use in therapy.

63. A method for producing a population of T cells suitable for augmenting or supporting T cell growth in vivo, comprising:
   a) activating the population of T cells by contacting the T cells in vitro with an anti-CD3 antibody or a CD3-binding fragment thereof, which is attached on a surface; and
   b) stimulating a CD28 accessory molecule on the surface of the T cells in vitro with an anti-CD28 antibody or a CD28-binding fragment thereof, wherein said anti-CD28 antibody or CD28-binding fragment thereof is attached on the same surface as the anti-CD3 antibody or CD3-binding fragment thereof, the activating and stimulating steps thereby producing a population of T cells suitable for augmenting or supporting T cell growth in vivo.

64. The method of claim 8, wherein the anti-CD28 antibody is 9.3, produced by hybridoma cell line ATCC No. HB10271.

65. The method of claim 37, wherein the anti-CD28 antibody is 9.3, produced by hybridoma cell line ATCC No. HB10271.

* * * * *